(12) United States Patent
Ryde et al.

(10) Patent No.: US 7,276,249 B2
(45) Date of Patent: Oct. 2, 2007

(54) NANOPARTICULATE FIBRATE FORMULATIONS

(75) Inventors: Tuula Ryde, Malvern, PA (US); Evan E. Gustow, Villanova, PA (US); Stephen B. Ruddy, Schwenksville, PA (US); Rajeev Jain, Collegeville, PA (US); Rakesh Patel, Bensalem, PA (US); Michael John Wilkins, Co. Cork (IE)

(73) Assignees: Elan Pharma International, Ltd., Athlone, Co. Westmeath (IE); Fournier Laboratories Ireland Ltd., Cork (IE)

( * ) Notice: Subject to any disclaimer, the term of this patent is extended or adjusted under 35 U.S.C. 154(b) by 0 days.

(21) Appl. No.: 10/444,066

(22) Filed: May 23, 2003

(65) Prior Publication Data
US 2005/0276974 A1    Dec. 15, 2005

Related U.S. Application Data

(63) Continuation-in-part of application No. 10/370,277, filed on Feb. 21, 2003.

(60) Provisional application No. 60/383,294, filed on May 24, 2002.

(51) Int. Cl.
*A61K 9/48*   (2006.01)
*A61K 9/20*   (2006.01)
*A61K 9/14*   (2006.01)

(52) U.S. Cl. .................. 424/451; 424/458; 424/464; 424/469; 424/470; 424/489; 424/490

(58) Field of Classification Search ................ 424/451, 424/458, 464, 469, 470, 489, 490
See application file for complete search history.

(56) References Cited

U.S. PATENT DOCUMENTS

| | | |
|---|---|---|
| 3,907,792 A | 9/1975 | Mieville |
| 4,250,191 A | 2/1981 | Edwards |
| 4,499,289 A | 2/1985 | Baran et al. |
| 4,540,602 A | 9/1985 | Motoyama et al. |
| 4,562,069 A | 12/1985 | Hegasy et al. |
| 4,647,576 A | 3/1987 | Hoefle et al. |
| 4,686,237 A | 8/1987 | Anderson |
| 4,783,484 A | 11/1988 | Violante et al. |
| 4,814,175 A | 3/1989 | Tack et al. |
| 4,826,689 A | 5/1989 | Violanto et al. |
| 4,895,726 A | 1/1990 | Curtet et al. |
| 4,997,454 A | 3/1991 | Violante et al. |

(Continued)

FOREIGN PATENT DOCUMENTS

EP    0 142 146 A2    5/1985

(Continued)

OTHER PUBLICATIONS

*The Physicians' Desk Reference*, 56th Ed., pp. 513-516 (2002).

(Continued)

*Primary Examiner*—Johann Richter
(74) *Attorney, Agent, or Firm*—Foley & Lardner LLP

(57) ABSTRACT

The present invention is directed to fibrate compositions having improved pharmacokinetic profiles and reduced fed/fasted variability. The fibrate particles of the composition have an effective average particle size of less than about 2000 nm.

189 Claims, 2 Drawing Sheets

U.S. PATENT DOCUMENTS

| | | |
|---|---|---|
| 5,145,684 A | 9/1992 | Liversidge et al. |
| 5,298,262 A | 3/1994 | Na et al. |
| 5,302,401 A | 4/1994 | Liversidge et al. |
| 5,318,767 A | 6/1994 | Liversidge et al. |
| 5,326,552 A | 7/1994 | Na et al. |
| 5,328,404 A | 7/1994 | Bacon |
| 5,336,507 A | 8/1994 | Na et al. |
| 5,340,564 A | 8/1994 | Illig et al. |
| 5,346,702 A | 9/1994 | Na et al. |
| 5,349,957 A | 9/1994 | Yudelson |
| 5,352,459 A | 10/1994 | Hollister et al. |
| 5,356,467 A | 10/1994 | Oshlack et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,238 A | 6/1996 | Bacon et al. |
| 5,534,270 A | 7/1996 | De Castro |
| 5,543,133 A | 8/1996 | Swanson et al. |
| 5,545,628 A | 8/1996 | Deboeck et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,622,938 A | 4/1997 | Wong |
| 5,628,981 A | 5/1997 | Liversidge et al. |
| 5,643,552 A | 7/1997 | Illig |
| 5,662,883 A | 9/1997 | Bagchi et al. |
| 5,665,331 A | 9/1997 | Bagchi et al. |
| 5,718,388 A | 2/1998 | Czekai et al. |
| 5,718,919 A | 2/1998 | Ruddy et al. |
| 5,741,522 A | 4/1998 | Violante et al. |
| 5,747,001 A | 5/1998 | Wiedmann et al. |
| 5,776,496 A | 7/1998 | Violante et al. |
| 5,834,025 A | 11/1998 | De Garavilla et al. |
| 5,862,999 A | 1/1999 | Czekai et al. |
| 6,045,829 A | 4/2000 | Liversidge et al. |
| 6,068,858 A | 5/2000 | Liversidge et al. |
| 6,074,670 A | 6/2000 | Stamm et al. |
| 6,124,322 A | 9/2000 | Bjoerkman et al. |
| 6,154,484 A | 11/2000 | Lee et al. |
| 6,177,103 B1 | 1/2001 | Pace et al. |
| 6,180,138 B1 | 1/2001 | Engh et al. |
| 6,221,400 B1 | 4/2001 | Liversidge et al. |
| 6,264,922 B1 | 7/2001 | Wood et al. |
| 6,270,806 B1 | 8/2001 | Liversidge et al. |
| 6,277,405 B1 | 8/2001 | Stamm et al. |
| 6,316,029 B1 | 11/2001 | Jain et al. |
| 6,368,620 B2 * | 4/2002 | Liu et al. ................ 424/451 |
| 6,368,622 B2 | 4/2002 | Chen et al. |
| 6,372,251 B2 | 4/2002 | Liu et al. |
| 6,375,986 B1 | 4/2002 | Ryde et al. |
| 6,383,517 B1 | 5/2002 | Qiu et al. |
| 6,384,062 B1 | 5/2002 | Ikeda et al. |
| 6,387,409 B1 | 5/2002 | Khan et al. |
| 6,428,814 B1 | 8/2002 | Bosch |
| 6,431,478 B1 | 8/2002 | Reed et al. |
| 6,432,381 B2 | 8/2002 | Liversidge et al. |
| 6,444,225 B1 | 9/2002 | Sherman |
| 6,451,339 B2 | 9/2002 | Patel et al. |
| 6,465,011 B2 | 10/2002 | Law et al. |
| 6,589,552 B2 | 7/2003 | Stamm et al. |
| 6,592,903 B2 | 7/2003 | Ryde et al. |
| 6,596,317 B2 | 7/2003 | Stamm et al. |
| 6,604,698 B2 | 8/2003 | Verhoff et al. |
| 6,634,576 B2 | 10/2003 | Verhoff et al. |
| 6,696,084 B2 * | 2/2004 | Pace et al. ................ 424/451 |
| 2001/0006658 A1 | 7/2001 | Liu et al. |
| 2001/0053385 A1 | 12/2001 | Lipari et al. |
| 2002/0012675 A1 | 1/2002 | Jain et al. |
| 2002/0012704 A1 | 1/2002 | Pace et al. |
| 2002/0056206 A1 | 5/2002 | Pace et al. |
| 2003/0031705 A1 | 2/2003 | Sherman |
| 2003/0077297 A1 | 4/2003 | Chen et al. |
| 2003/0194442 A1 | 10/2003 | Guivarch et al. |
| 2004/0058009 A1* | 3/2004 | Ryde et al. ................ 424/490 |

FOREIGN PATENT DOCUMENTS

| | | |
|---|---|---|
| EP | 0 221 025 A1 | 5/1987 |
| EP | 1 112 064 B1 | 7/2001 |
| GB | 2 166 651 A | 5/1986 |
| WO | WO 86/03488 A1 | 6/1986 |
| WO | WO 86/07054 A1 | 12/1986 |
| WO | WO 99/29300 * | 6/1999 |
| WO | WO 99/29300 A1 | 6/1999 |
| WO | WO 00/16749 A1 | 3/2000 |
| WO | WO 00/37057 A2 | 6/2000 |
| WO | WO 00/57859 A1 | 10/2000 |
| WO | WO 00/57918 A2 | 10/2000 |
| WO | WO 00/72829 A1 | 12/2000 |
| WO | WO 01/21154 A2 | 3/2001 |
| WO | WO 01/85345 A1 | 11/2001 |
| WO | WO 02/17883 A2 | 3/2002 |
| WO | WO 02/24169 A1 | 3/2002 |
| WO | WO 02/24192 A1 | 3/2002 |
| WO | WO 02/24193 A1 | 3/2002 |
| WO | WO 02/067901 A1 | 9/2002 |
| WO | WO 02/098565 A1 | 12/2002 |
| WO | WO 03/013474 A1 | 2/2003 |
| WO | WO 03/013500 A1 | 2/2003 |

OTHER PUBLICATIONS

Lindahl et al., "Characterization of Fluids from the Stomach and Proximal Jejunum in Men and Women," *Pharm. Res.*, 14(4): 497-502 (1997).

Guivarc'h et al., "A New Fenofibrate Formulation: Results of Six Single-Dose, Clinical Studies of Bioavailablity Under Fed and Fasting Conditions," *Clinical Therapeutics*, vol. 26, No. 9, 2004, pp. 1456-1469.

Guidance for Industry, Levothyroxine Sodium Tablets-In Vivo Pharmacokinetic and Bioavailability Studies and in Vitro Dissolution Testing, U.S. Department of Health and Human Services, Food and Drug Administration, Dec. 2000, pp. 1-8.

* cited by examiner

US 7,276,249 B2

NANOPARTICULATE FIBRATE FORMULATIONS

CROSS REFERENCE TO RELATED APPLICATIONS

This application is a continuation-in-part of U.S. patent application Ser. No. 10/370,277, filed on Feb. 21, 2003, currently pending, which claims priority of U.S. Provisional Application No. 60/383,294, filed on May 24, 2002.

FIELD OF THE INVENTION

The present invention relates to a nanoparticulate composition comprising a fibrate, preferably fenofibrate or a salt thereof. The nanoparticulate fibrate, preferably fenofibrate, particles have an effective average particle size of less than about 2000 nm.

BACKGROUND OF THE INVENTION

A. Background Regarding Nanoparticulate Compositions

Nanoparticulate compositions, first described in U.S. Pat. No. 5,145,684 ("the '684 patent"), are particles consisting of a poorly soluble therapeutic or diagnostic agent having adsorbed onto the surface thereof a non-crosslinked surface stabilizer. The '684 patent does not describe nanoparticulate compositions of a fibrate.

Methods of making nanoparticulate compositions are described in, for example, U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Nonionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anhydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly (ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive Nanoparticulate Compositions Having Cationic Surface Stabilizers;" U.S. Pat. No. 6,431,478 for "Small Scale Mill;" and U.S. Pat. No. 6,432,381 for "Methods for Targeting Drug Delivery to the Upper and/or Lower Gastrointestinal Tract," all of which are specifically incorporated by reference. In addition, U.S. patent application No. 20020012675 A1, published on Jan. 31, 2002, for "Controlled Release Nanoparticulate Compositions," describes nanoparticulate compositions, and is specifically incorporated by reference.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

B. Background Regarding Fenofibrate

The compositions of the invention comprise a fibrate, preferably fenofibrate. Fenofibrate, also known as 2-[4-(4-chlorobenzoyl)phenoxy]-2-methyl-propanoic acid, 1-methylethyl ester, is a lipid regulating agent. The compound is insoluble in water. See *The Physicians' Desk Reference, 56th* Ed., pp. 513-516 (2002).

Fenofibrate is described in, for example, U.S. Pat. No. 3,907,792 for "Phenoxy-Alkyl-Carboxylic Acid Derivatives and the Preparation Thereof;" U.S. Pat. No. 4,895,726 for "Novel Dosage Form of Fenofibrate;" U.S. Pat. Nos. 6,074,670 and 6,277,405, both for "Fenofibrate Pharmaceutical Composition Having High Bioavailability and Method for Preparing It." U.S. Pat. No. 3,907,792 describes a class of phenoxy-alkyl carboxylic compounds which encompasses fenofibrate. U.S. Pat. No. 4,895,726 describes a gelatin capsule therapeutic composition, useful in the oral treatment of hyerlipidemia and hypercholesterolemia, containing micronized fenofibrate. U.S. Pat. No. 6,074,670 refers to immediate-release fenofibrate compositions comprising micronized fenofibrate and at least one inert hydrosoluble carrier. U.S. Pat. No. 4,739,101 describes a process for making fenofibrate. U.S. Pat. No. 6,277,405 is directed to micronized fenofibrate compositions having a specified dissolution profile. In addition, International Publication No. WO 02/24193 for "Stabilised Fibrate Microparticles," published on Mar. 28, 2002, describes a microparticulate fenofibrate composition comprising a phospholipid. Finally, International Publication No. WO 02/067901 for "Fibrate-Statin Combinations with Reduced Fed-Fasted Effects," published on Sep. 6, 2002, describes a microparticulate fenofibrate composition comprising a phospholipid and a hydroxymethylglutaryl coenzyme A (HMG-CoA) reductase inhibitor or statin.

WO 01/80828 for "Improved Water-Insoluble Drug Particle Process," and International Publication No. WO 02/24193 for "Stabilised Fibrate Microparticles," describe a process for making small particle compositions of poorly water soluble drugs. The process requires preparing an admixture of a drug and one or more surface active agents, followed by heating the drug admixture to at or above the melting point of the poorly water soluble drug. The heated suspension is then homogenized. The use of such a heating process is undesirable, as heating a drug to its melting point destroys the crystalline structure of the drug. Upon cooling, a drug may be amorphous or recrystallize in a different isoform, thereby producing a composition which is physically and structurally different from that desired. Such a "different" composition may have different pharmacological properties. This is significant as U.S. Food and Drug Administration (USFDA) approval of a drug substance requires that the drug substance be stable and produced in a repeatable process.

WO 03/013474 for "Nanoparticulate Formulations of Fenofibrate," published on Feb. 20, 2003, describes fibrate compositions comprising vitamin E TGPS (polyethylene glycol (PEG) derivatized vitamin E). The fibrate compositions of this reference comprise particles of fibrate and vitamin E TPGS having a mean diameter from about 100 nm to about 900 nm (page 8, lines 12-15, of WO 03/013474), a $D_{50}$ of 350-750 nm, and a $D_{99}$ of 500 to 900 nm (page 9, lines 11-13, of WO 03/013474) (50% of the particles of a composition fall below a "$D_{50}$", and 99% of the particles of a composition fall below a $D_{99}$). The reference does not teach that the described compositions show minimal or no variability when administered in fed as compared to fasted conditions.

A variety of clinical studies have demonstrated that elevated levels of total cholesterol (total-C), low density lipoprotein cholesterol (LDL-C), and apolipoprotein B (apo B), an LDL membrane complex, are associated with human atherosclerosis. Similarly, decreased levels of high density lipoprotein cholesterol (HDL-C) and its transport complex, apolipoprotein A (apo A2 and apo AII), are associated with the development of atherosclerosis. Epidemiologic investigations have established that cardiovascular morbidity and mortality vary directly with the level of total-C, LDL-C, and triglycerides, and inversely with the level of HDL-C.

Fenofibric acid, the active metabolite of fenofibrate, produces reductions in total cholesterol, LDL cholesterol, apolipoprotein B, total triglycerides, and triglyceride rich lipoprotein (VLDL) in treated patients. In addition, treatment with fenofibrate results in increases in high density lipoprotein (HDL) and apolipoprotein apoAI and apoAII. See *The Physicians' Desk Reference, 56th* Ed., pp. 513-516 (2002).

Because fibrates, including fenofibrate, are so insoluble in water, significant bioavailability can be problematic. In addition, conventional fibrate, including fenofibrate, formulations exhibit dramatically different effects depending upon the fed or fasted state of the patient. Finally, conventional fibrate, including fenofibrate, formulations require relatively large doses to achieve the desired therapeutic effects. There is a need in the art for nanoparticulate fibrate formulations which overcome these and other problems associated with prior conventional microcrystalline fibrate formulations. The present invention satisfies these needs.

SUMMARY OF THE INVENTION

The present invention relates to nanoparticulate compositions comprising a fibrate, preferably fenofibrate. The compositions comprise a fibrate, preferably fenofibrate, and at least one surface stabilizer adsorbed on the surface of the fibrate particles. The nanoparticulate fibrate, preferably fenofibrate, particles have an effective average particle size of less than about 2000 nm.

A preferred dosage form of the invention is a solid dosage form, although any pharmaceutically acceptable dosage form can be utilized.

Another aspect of the invention is directed to pharmaceutical compositions comprising a nanoparticulate fibrate, preferably fenofibrate, composition of the invention. The pharmaceutical compositions comprise a fibrate, preferably fenofibrate, at least one surface stabilizer, and a pharmaceutically acceptable carrier, as well as any desired excipients.

One embodiment of the invention encompasses a fibrate, preferably fenofibrate, composition, wherein the pharmacokinetic profile of the fibrate is not affected by the fed or fasted state of a subject ingesting the composition, in particular as defined by $C_{max}$ and AUC guidelines given by the U.S. Food and Drug Administration and the corresponding European regulatory agency (EMEA).

Another aspect of the invention is directed to a nanoparticulate fibrate, preferably fenofibrate, composition having improved pharmacokinetic profiles as compared to conventional microcrystalline fibrate formulations, such as $T_{max}$, $C_{max}$, and AUC.

In yet another embodiment, the invention encompasses a fibrate, preferably fenofibrate, composition, wherein administration of the composition to a subject in a fasted state is bioequivalent to administration of the composition to a subject in a fed state, in particular as defined by $C_{max}$ and AUC guidelines given by the U.S. Food and Drug Administration and the corresponding European regulatory agency (EMEA).

Another embodiment of the invention is directed to nanoparticulate fibrate, preferably fenofibrate, compositions additionally comprising one or more compounds useful in treating dyslipidemia, hyperlipidemia, hypercholesterolemia, cardiovascular disorders, or related conditions.

Other embodiments of the invention include, but are not limited to, nanoparticulate fibrate, preferably fenofibrate, formulations which, as compared to conventional non-nanoparticulate formulations of a fibrate, particularly a fenofibrate such as TRICOR® (160 mg tablet or 200 mg capsule microcrystalline fenofibrate formulations), have one or more of the following properties: (1) smaller tablet or other solid dosage form size; (2) smaller doses of drug required to obtain the same pharmacological effect; (3) increased bioavailability; (4) substantially similar pharmacokinetic profiles of the nanoparticulate fibrate, preferably fenofibrate, compositions when administered in the fed versus the fasted state; (5) an increased rate of dissolution for the nanoparticulate fibrate, preferably fenofibrate, compositions; and (6) bioadhesive fibrate, preferably fenofibrate, compositions.

This invention further discloses a method of making a nanoparticulate fibrate, preferably fenofibrate, composition according to the invention. Such a method comprises contacting a fibrate, preferably fenofibrate, and at least one surface stabilizer for a time and under conditions sufficient to provide a nanoparticulate fibrate composition, and preferably a fenofibrate composition. The one or more surface stabilizers can be contacted with a fibrate, preferably fenofibrate, either before, during, or after size reduction of the fibrate.

The present invention is also directed to methods of treatment using the nanoparticulate fibrate, preferably fenofibrate, compositions of the invention for conditions such as hypercholesterolemia, hypertriglyceridemia, coronary heart disease, and peripheral vascular disease (including symptomatic carotid artery disease). The compositions of the invention can be used as adjunctive therapy to diet for the reduction of LDL-C, total-C, triglycerides, and Apo B in adult patients with primary hypercholesterolemia or mixed dyslipidemia (Fredrickson Types IIa and IIb). The compositions can also be used as adjunctive therapy to diet for treatment of adult patients with hypertriglyceridemia (Fredrickson Types IV and V hyperlipidemia). Markedly elevated levels of serum tryglycerides (e.g., >2000 mg/dL) may increase the risk of developing pancreatitis. Such methods comprise administering to a subject a therapeutically effective amount of a nanoparticulate fibrate, preferably fenofibrate, composition according to the invention. Other methods of treatment using the nanoparticulate compositions of the invention are know to those of skill in the art.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

Figure 1:
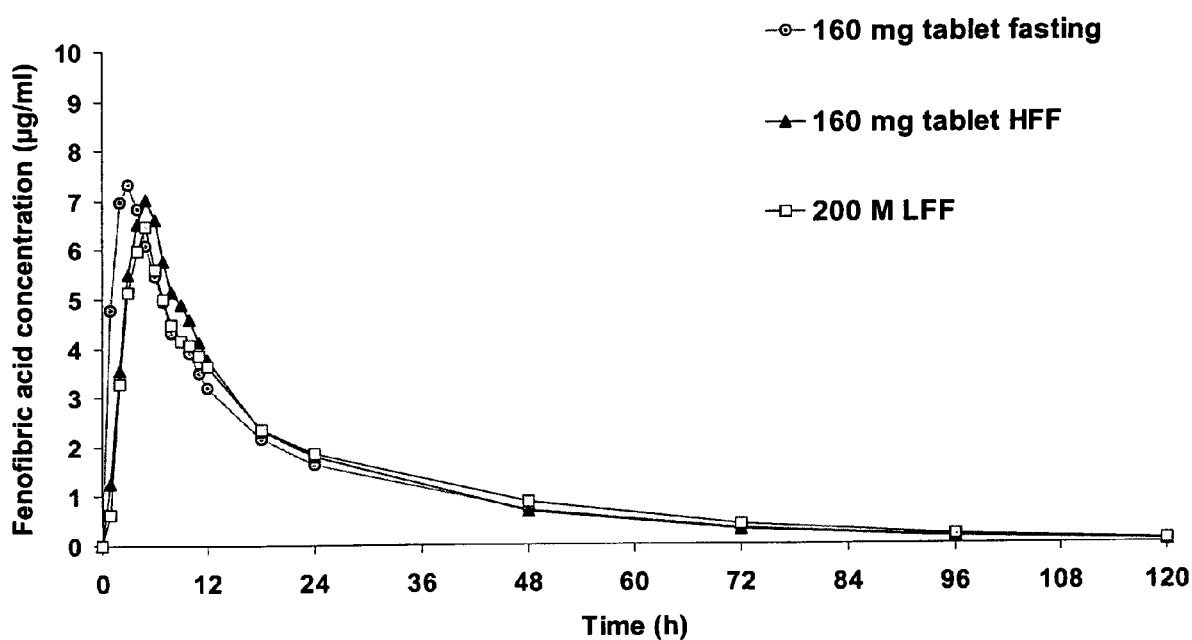
FIG. 1: Shows the fenofibric acid concentration (μg/ml) over a period of 120 minutes for a single dose of: (a) a 160 mg nanoparticulate fenofibrate tablet administered to a fasting subject; (b) a 160 mg nanoparticulate fenofibrate tablet administered to a high fat fed subject; and (c) a 200 mg microcrystalline (TRICOR®; Abbott Laboratories, Abbott Park, Ill.) capsule administered to a low fat fed subject.

The present invention is directed to nanoparticulate compositions comprising a fibrate, preferably fenofibrate. The compositions comprise a fibrate, preferably fenofibrate, and preferably at least one surface stabilizer adsorbed on the surface of the drug. The nanoparticulate fibrate, preferably fenofibrate, particles have an effective average particle size of less than about 2000 nm.

As taught in the '684 patent, and as exemplified in the examples below, not every combination of surface stabilizer and active agent will result in a stable nanoparticulate composition. It was surprisingly discovered that stable, nanoparticulate fibrate, preferably fenofibrate, formulations can be made.

Advantages of the nanoparticulate fibrate, preferably fenofibrate, formulations of the invention as compared to conventional non-nanoparticulate formulations of a fibrate, particularly a fenofibrate such as TRICOR® (tablet or capsule microcrystalline fenofibrate formulations), include, but are not limited to: (1) smaller tablet or other solid dosage form size; (2) smaller doses of drug required to obtain the same pharmacological effect; (3) increased bioavailability; (4) substantially similar pharmacokinetic profiles of the nanoparticulate fibrate, preferably fenofibrate, compositions when administered in the fed versus the fasted state; (5) improved pharmacokinetic profiles; (6) bioequivalency of the nanoparticulate fibrate, preferably fenofibrate, compositions when administered in the fed versus the fasted state; (7) an increased rate of dissolution for the nanoparticulate fibrate, preferably fenofibrate, compositions; (8) bioadhesive fibrate, preferably fenofibrate, compositions; and (9) the nanoparticulate fibrate, preferably fenofibrate, compositions can be used in conjunction with other active agents useful in treating dyslipidemia, hyperlipidemia, hypercholesterolemia, cardiovascular disorders, or related conditions.

The present invention also includes nanoparticulate fibrate, preferably fenofibrate, compositions together with one or more non-toxic physiologically acceptable carriers, adjuvants, or vehicles, collectively referred to as carriers. The compositions can be formulated for parenteral injection (e.g., intravenous, intramuscular, or subcutaneous), oral administration in solid, liquid, or aerosol form, vaginal, nasal, rectal, ocular, local (powders, ointments or drops), buccal, intracisternal, intraperitoneal, or topical administration, and the like.

A preferred dosage form of the invention is a solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof. A solid dose tablet formulation is preferred.

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein with reference to stable fibrate, preferably fenofibrate, particles, "stable" includes, but is not limited to, one or more of the following parameters: (1) that the fibrate particles do not appreciably flocculate or agglomerate due to interparticle attractive forces, or otherwise significantly increase in particle size over time; (2) that the physical structure of the fibrate, preferably fenofibrate, particles is not altered over time, such as by conversion from an amorphous phase to crystalline phase; (3) that the fibrate, preferably fenofibrate, particles are chemically stable; and/or (4) where the fibrate has not been subject to a heating step at or above the melting point of the fibrate in the preparation of the nanoparticles of the invention.

A. Preferred Characteristics of the Fibrate Compositions of the Invention

1. Increased Bioavailability

The fibrate, preferably fenofibrate, formulations of the invention exhibit increased bioavailability, at the same dose of the same fibrate, and require smaller doses as compared to prior conventional fibrate, preferably fenofibrate, formulations.

For example, as shown below in Example 6, administration of a 160 mg nanoparticulate fenofibrate tablet in a fasted state is not bioequivalent to administration of a 200 mg conventional microcrystalline fenofibrate capsule (TRICOR®) in a fed state, pursuant to regulatory guidelines. Under U.S. FDA guidelines, two products or methods are bioequivalent if the 90% Confidence Intervals (CI) for AUC and $C_{max}$ are between 0.80 to 1.25 ($T_{max}$ measurements are not relevant to bioequivalence for regulatory purposes). To show bioequivalency between two compounds or administration conditions pursuant to Europe's EMEA guidelines, the 90% CI for AUC must be between 0.80 to 1.25 and the 90% CI for $C_{max}$ must between 0.70 to 1.43.

The non-bioequivalence is significant because it means that the nanoparticulate fenofibrate dosage form exhibits significantly greater drug absorption. For the nanoparticulate fenofibrate dosage form to be bioequivalent to the conventional microcrystalline fenofibrate dosage form (e.g., TRICOR®) the nanoparticulate fenofibrate dosage form would have to contain significantly less drug. Thus, the nanoparticulate fenofibrate dosage form significantly increases the bioavailability of the drug.

Moreover, as shown below in Example 6, administration of a 160 mg nanoparticulate fenofibrate tablet in a fed state is bioequivalent to administration of a 200 mg conventional microcrystalline fenofibrate capsule (TRICOR®) in a fed state. Thus, the nanoparticulate fenofibrate dosage form requires less drug to obtain the same pharmacological effect observed with the conventional microcrystalline fenofibrate dosage form (e.g., TRICOR®). Therefore, the nanoparticulate fenofibrate dosage form has an increased bioavailability as compared to the conventional microcrystalline fenofibrate dosage form (e.g., TRICOR®).

Greater bioavailability of the fibrate compositions of the invention can enable a smaller solid dosage size. This is particularly significant for patient populations such as the elderly, juvenile, and infant. In one embodiment of the invention, disclosed is a stable solid dose fenofibrate composition comprising: (a) a therapeutically effective dosage of 145 mg of particles of fenofibrate or a salt thereof; and (b) associated with the surface thereof at least one surface stabilizer. Characteristics of the composition include: (i) the fenofibrate particles have an effective average particle size of less than about 2000 nm; (ii) the solid dose is bioequivalent to the TRICOR® 160 mg tablet, wherein bioequivalency is established by a 90% Confidence Interval of between 0.80 and 1.25 for both $C_{max}$ and AUC or a 90% Confidence Interval of between 0.80 and 1.25 for AUC and a 90% Confidence Interval of between 0.70 to 1.43 for $C_{max}$; and (iii) the solid dose is about 10% smaller than the TRICOR® tablet. In another embodiment of the invention, disclosed is a stable solid dose fenofibrate composition comprising: (a) a therapeutically effective dosage of 48 mg of particles of fenofibrate or a salt thereof; and (b) associated with the surface thereof at least one surface stabilizer. Characteristics of the composition include: (i) the fenofibrate particles have an effective average particle size of less than about 2000 nm; (ii) the solid dose is bioequivalent to the TRICOR® 54 mg tablet, wherein bioequivalency is established by a 90% Confidence Interval of between 0.80 and 1.25 for both $C_{max}$ and AUC or a 90% Confidence Interval of between 0.80 and 1.25 for AUC and a 90%

Confidence Interval of between 0.70 to 1.43 for $C_{max}$; and (iii) the solid dose is about 10% smaller than the TRICOR® tablet.

2. Improved Pharmacokinetic Profiles

The invention also provides fibrate, preferably fenofibrate, compositions having a desirable pharmacokinetic profile when administered to mammalian subjects. The desirable pharmacokinetic profile of the fibrate, preferably fenofibrate, compositions comprise the parameters: (1) that the $T_{max}$ of a fibrate, preferably fenofibrate, when assayed in the plasma of the mammalian subject, is less than about 6 to about 8 hours. Preferably, the $T_{max}$ parameter of the pharmacokinetic profile is less than about 6 hours, less than about 5 hours, less than about 4 hours, less than about 3 hours, less than about 2 hours, less than about 1 hour, or less than about 30 minutes after administration. The desirable pharmacokinetic profile, as used herein, is the pharmacokinetic profile measured after the initial dose of a fibrate, preferably fenofibrate. The compositions can be formulated in any way as described below and as known to those of skill in the art.

Current marketed formulations of fenofibrate include tablets, ice., TRICOR® tablets marketed by Abbott Laboratories. According to the description of TRICOR®, the pharmacokinetic profile of the tablets contain parameters such that the median $T_{max}$ is 6-8 hours (Physicians Desk Reference, 56$^{th}$ Ed., 2002). Because the compound is virtually insoluble in water, the absolute bioavailability of TRICOR® cannot be determined (Physicians Desk Reference, 56$^{th}$ Ed., 2002). The compositions of the invention improve upon at least the $T_{max}$ parameter of the pharmacokinetic profile of a fibrate, preferably fenofibrate.

A preferred fibrate formulation, preferably a fenofibrate formulation, of the invention exhibits in comparative pharmacokinetic testing with a standard commercial formulation of the same fibrate, e.g., TRICOR® tablets from Abbott Laboratories for fenofibrate, a $T_{max}$ not greater than about 90%, not greater than about 80%, not greater than about 70%, not greater than about 60%, not greater than about 50%, not greater than about 30%, or not greater than about 25% of the $T_{max}$ exhibited by a standard commercial fibrate formulation, e.g., TRICOR® tablets for fenofibrate.

Any formulation giving the desired pharmacokinetic profile is suitable for administration according to the present methods. Exemplary types of formulations giving such profiles are liquid dispersions, gels, aerosols, ointments, creams, solid dose forms, etc. of a nanoparticulate fibrate, preferably nanoparticulate fenofibrate.

In a preferred embodiment of the invention, a fenofibrate composition of the invention comprises fenofibrate or a salt thereof, which when administered to a human as a dose of about 160 mg presents an AUC of about 139 μg/mL.h.

In yet another preferred embodiment of the invention, a fenofibrate composition of the invention comprises fenofibrate and has a $C_{max}$ under fasted conditions which is greater than the $C_{max}$ under high fat fed (HFF) conditions, when administered to a human.

3. The Pharmacokinetic Profiles of the Fibrate Compositions of the Invention are not Affected by the Fed or Fasted State of the Subject Ingesting the Compositions The invention encompasses a fibrate, preferably fenofibrate, composition wherein the pharmacokinetic profile of the fibrate is not substantially affected by the fed or fasted state of a subject ingesting the composition, when administered to a human. This means that there is no substantial difference in the quantity of drug absorbed or the rate of drug absorption when the nanoparticulate fibrate, preferably fenofibrate, compositions are administered in the fed versus the fasted state.

For conventional fenofibrate formulations, i.e., TRICOR®, the absorption of fenofibrate is increased by approximately 35% when administered with food. This significant difference in absorption observed with conventional fenofibrate formulations is undesirable. The fibrate, preferably fenofibrate, formulations of the invention overcome this problem, as the fibrate formulations reduce or preferably substantially eliminate significantly different absorption levels when administered under fed as compared to fasting conditions when administered to a human.

In a preferred embodiment of the invention, a fenofibrate composition of the invention comprises about 145 mg of fenofibrate and exhibits minimal or no food effect when administered to a human. In another preferred embodiment of the invention, a fenofibrate composition of the invention comprises about 48 mg of fenofibrate and exhibits minimal or no food effect when administered to a human.

As shown in Example 6, the pharmacokinetic parameters of the fenofibrate compositions of the invention are the same when the composition is administered in the fed and fasted states when administered to a human. Specifically, there was no substantial difference in the rate or quantity of drug absorption when the fenofibrate composition was administered in the fed versus the fasted state. Thus, the fibrate compositions, and preferably fenofibrate compositions, of the invention substantially eliminate the effect of food on the pharmacokinetics of the fibrate when administered to a human.

Benefits of a dosage form which substantially eliminates the effect of food include an increase in subject convenience, thereby increasing subject compliance, as the subject does not need to ensure that they are taking a dose either with or without food. This is significant, as with poor subject compliance an increase in the medical condition for which the drug is being prescribed may be observed, i.e., cardiovascular problems for poor subject compliance with a fibrate such as fenofibrate.

4. Bioequivalency of the Fibrate Compositions of the Invention When Administered in the Fed Versus the Fasted State The invention also encompasses a fibrate, preferably a fenofibrate, composition in which administration of the composition to a subject in a fasted state is bioequivalent to administration of the composition to a subject in a fed state. "Bioequivalency" is established by a 90% Confidence Interval (CI) of between 0.80 and 1.25 for both $C_{max}$ and AUC under USFDA regulatory guidelines, or a 90% CI for AUC of between 0.80 to 1.25 and a 90% CI for $C_{max}$ of between 0.70 to 1.43 under the European EMEA regulatory guidelines.

The difference in absorption of the fibrate, preferably fenofibrate, compositions of the invention, when administered in the fed versus the fasted state, preferably is less than about 35%, less than about 30%, less than about 25%, less than about 20%, less than about 15%, less than about 10%, less than about 5%, or less than about 3%.

As shown in Example 6, administration of a fenofibrate composition according to the invention in a fasted state was bioequivalent to administration of a fenofibrate composition according to the invention in a fed state, pursuant to regulatory guidelines. Under USFDA guidelines, two products or methods are bioequivalent if the 90% Confidence Intervals (CI) for $C_{max}$ (peak concentration) and the AUC (area under the concentration/time curve) are between 0.80 to 1.25. For Europe, the test for bioequivalency is if two products or methods have a 90% CI for AUC of between 0.80 to 1.25 and a 90% CI for $C_{max}$ of between 0.70 to 1.43. The fibrate, preferably fenofibrate, compositions of the invention meet both the U.S. and European guidelines for bioequivalency for administration in the fed versus the fasted state.

5. Dissolution Profiles of the Fibrate Compositions of the Invention

The fibrate, preferably fenofibrate, compositions of the invention have unexpectedly dramatic dissolution profiles. Rapid dissolution of an administered active agent is preferable, as faster dissolution generally leads to faster onset of action and greater bioavailability. To improve the dissolution profile and bioavailability of fibrates, and in particulate fenofibrate, it would be useful to increase the drug's dissolution so that it could attain a level close to 100%.

The fibrate, preferably fenofibrate, compositions of the invention preferably have a dissolution profile in which within about 5 minutes at least about 20% of the composition is dissolved. In other embodiments of the invention, at least about 30% or about 40% of the fibrate, preferably fenofibrate, composition is dissolved within about 5 minutes. In yet other embodiments of the invention, preferably at least about 40%, about 50%, about 60%, about 70%, or about 80% of the fibrate, preferably fenofibrate, composition is dissolved within about 10 minutes. Finally, in another embodiment of the invention, preferably at least about 70%, about 80%, about 90%, or about 100% of the fibrate, preferably fenofibrate, composition is dissolved within about 20 minutes.

Dissolution is preferably measured in a medium which is discriminating. Such a dissolution medium will produce two very different dissolution curves for two products having very different dissolution profiles in gastric juices; i.e., the dissolution medium is predictive of in vivo dissolution of a composition. An exemplary dissolution medium is an aqueous medium containing the surfactant sodium lauryl sulfate at 0.025 M. Determination of the amount dissolved can be carried out by spectrophotometry. The rotating blade method (European Pharmacopoeia) can be used to measure dissolution.

6. Redispersibility Profiles of the Fibrate Compositions of the Invention

An additional feature of the fibrate, preferably fenofibrate, compositions of the invention is that the compositions redisperse such that the effective average particle size of the redispersed fibrate particles is less than about 2 microns. This is significant, as if upon administration the nanoparticulate fibrate compositions of the invention did not redisperse to a substantially nanoparticulate particle size, then the dosage form may lose the benefits afforded by formulating the fibrate into a nanoparticulate particle size.

This is because nanoparticulate active agent compositions benefit from the small particle size of the active agent; if the active agent does not redisperse into the small particle sizes upon administration, then "clumps" or agglomerated active agent particles are formed, owing to the extremely high surface free energy of the nanoparticulate system and the thermodynamic driving force to achieve an overall reduction in free energy. With the formation of such agglomerated particles, the bioavailability of the dosage form may fall well below that observed with the liquid dispersion form of the nanoparticulate active agent.

Moreover, the nanoparticulate fibrate, preferably fenofibrate, compositions of the invention exhibit dramatic redispersion of the nanoparticulate fibrate particles upon administration to a mammal, such as a human or animal, as demonstrated by reconstitution/redispersion in a biorelevant aqueous media such that the effective average particle size of the redispersed fibrate particles is less than about 2 microns. Such biorelevant aqueous media can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1M while fasted state intestinal fluid has an ionic strength of about 0.14. See e.g., Lindahl et al., "Characterization of Fluids from the Stomach and Proximal Jejunum in Men and Women," *Pharm. Res.,* 14 (4): 497-502 (1997).

It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 M, and NaCl solutions, ranging in concentration from about 0.001 to about 0.1 M, and mixtures thereof. For example, electrolyte solutions can be, but are not limited to, about 0.1 M HCl or less, about 0.01 M HCl or less, about 0.001 M HCl or less, about 0.1 M NaCl or less, about 0.01 M NaCl or less, about 0.001 M NaCl or less, and mixtures thereof. Of these electrolyte solutions, 0.01 M HCl and/or 0.1 M NaCl, are most representative of fasted human physiological conditions, owing to the pH and ionic strength conditions of the proximal gastrointestinal tract.

Electrolyte concentrations of 0.001 M HCl, 0.01 M HCl, and 0.1 M HCl correspond to pH 3, pH 2, and pH 1, respectively. Thus, a 0.01 M HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+sodium, potassium and calcium salts of chloride.

In other embodiments of the invention, the redispersed fibrate, preferably fenofibrate, particles of the invention (redispersed in an aqueous, biorelevant, or any other suitable media) have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 run, less than about 250 nm, less than about 200 nm, less than about 150 nm, less than about 100 nm, less than about 75 nm, or less than about 50 nm, as measured by light-scattering methods, microscopy, or other appropriate methods.

Redispersibility can be tested using any suitable means known in the art. See e.g., the example sections of U.S. Pat. No. 6,375,986 for "Solid Dose Nanoparticulate Compositions Comprising a Synergistic Combination of a Polymeric Surface Stabilizer and Dioctyl Sodium Sulfosuccinate."

7. Bioadhesive Fibrate Compositions

Bioadhesive fibrate, particularly fenofibrate, compositions of the invention comprise at least one cationic surface stabilizer, which are described in more detail below. Bioadhesive formulations of fibrate, particularly fenofibrate, exhibit exceptional bioadhesion to biological surfaces, such as mucous. The term bioadhesion refers to any attractive interaction between two biological surfaces or between a biological and a synthetic surface. In the case of bioadhesive nanoparticulate compositions, the term bioadhesion is used to describe the adhesion between the nanoparticulate fibrate, particularly fenofibrate, compositions and a biological substrate (i.e. gastrointestinal mucin, lung tissue, nasal mucosa, etc.). See e.g., U.S. Pat. No. 6,428,814 for "Bioadhesive Nanoparticulate Compositions Having Cationic Surface Stabilizers," which is specifically incorporated by reference.

There are basically two mechanisms which may be responsible for this bioadhesion phenomena: mechanical or physical interactions and chemical interactions. The first of these, mechanical or physical mechanisms, involves the physical interlocking or interpenetration between a bioadhesive entity and the receptor tissue, resulting from a good wetting of the bioadhesive surface, swelling of the bioadhesive polymer, penetration of the bioadhesive entity into a crevice of the tissue surface, or interpenetration of bioadhesive composition chains with those of the mucous or other such related tissues. The second possible mechanism of bioadhesion incorporates forces such as ionic attraction, dipolar forces, van der Waals interactions, and hydrogen bonds. It is this form of bioadhesion which is primarily responsible for the bioadhesive properties of the nanoparticulate fibrate, preferably fenofibrate, compositions of the invention. However, physical and mechanical interactions may also play a secondary role in the bioadhesion of such nanoparticulate compositions.

The bioadhesive fibrate, preferably fenofibrate, compositions of the invention are useful in any situation in which it is desirable to apply the compositions to a biological surface. The bioadhesive fibrate, preferably fenofibrate, compositions coat the targeted surface in a continuous and uniform film which is invisible to the naked human eye.

A bioadhesive fibrate, preferably fenofibrate, composition slows the transit of the composition, and some fibrate particles would also most likely adhere to tissue other than the mucous cells and therefore give a prolonged exposure to the fibrate, thereby increasing absorption and the bioavailability of the administered dosage.

8. Fibrate Compositions Used in Conjunction with Other Active Agents

The fibrate, preferably fenofibrate, compositions of the invention can additionally comprise one or more compounds useful in treating dyslipidemia, hyperlipidemia, hypercholesterolemia, cardiovascular disorders, or related conditions, or the fibrate, preferably fenofibrate, compositions can be administered in conjunction with such a compound. Examples of such compounds include, but are not limited to, statins or HMG CoA reductase inhibitors and antihypertensives. Examples of antihypertensives include, but are not limited to diuretics ("water pills"), beta blockers, alpha blockers, alpha-beta blockers, sympathetic nerve inhibitors, angiotensin converting enzyme (ACE) inhibitors, calcium channel blockers, angiotensin receptor blockers (formal medical name angiotensin-2-receptor antagonists, known as "sartans" for short).

Examples of statins or HMG CoA reductase inhibitors include, but are not limited to, lovastatin; pravastatin; simavastatin; velostatin; atorvastatin (Lipitor®) and other 6-[2-(substituted-pyrrol-1-yl)alkyl]pyran-2-ones and derivatives, as disclosed in U.S. Pat. No. 4,647,576); fluvastatin (Lescol®); fluindostatin (Sandoz XU-62-320); pyrazole analogs of mevalonolactone derivatives, as disclosed in PCT application WO 86/03488; rivastatin and other pyridyldihydroxyheptenoic acids, as disclosed in European Patent 491226A; Searle's SC45355 (a 3-substituted pentanedioic acid derivative); dichloroacetate; imidazole analogs of mevalonolactone, as disclosed in PCT application WO 86107054; 3-carboxy-2-hydroxy-propane-phosphonic acid derivatives, as disclosed in French Patent No. 2,596,393; 2,3-di-substituted pyrrole, furan, and thiophene derivatives, as disclosed in European Patent Application No. 0221025; naphthyl analogs of mevalonolactone, as disclosed in U.S. Pat. No. 4,686,237; octahydronaphthalenes, such as those disclosed in U.S. Pat. No. 4,499,289; keto analogs of mevinolin (lovastatin), as disclosed in European Patent Application No. 0,142,146 A2; phosphinic acid compounds; as well as other HMG CoA reductase inhibitors.

B. Compositions

The invention provides compositions comprising fibrate, preferably fenofibrate, particles and at least one surface stabilizer. The surface stabilizers preferably are adsorbed on, or associated with, the surface of the fibrate, preferably fenofibrate, particles. Surface stabilizers especially useful herein preferably physically adhere on, or associate with, the surface of the nanoparticulate fibrate particles but do not chemically react with the fibrate particles or itself. Individually adsorbed molecules of the surface stabilizer are essentially free of intermolecular cross-linkages.

The present invention also includes fibrate, preferably fenofibrate, compositions together with one or more non-toxic physiologically acceptable carriers, adjuvants, or vehicles, collectively referred to as carriers. The compositions can be formulated for parenteral injection (e.g., intravenous, intramuscular, or subcutaneous), oral administration in solid, liquid, or aerosol form, vaginal, nasal, rectal, ocular, local (powders, ointments or drops), buccal, intracisternal, intraperitoneal, or topical administration, and the like.

1. Fibrate Particles

As used herein the term "fibrate" means any of the fibric acid derivatives useful in the methods described herein, e.g., fenofibrate. Fenofibrate is a fibrate compound, other examples of which are bezafibrate, beclobrate, binifibrate, ciplofibrate, clinofibrate, clofibrate, clofibric acid, etofibrate, gemfibrozil, nicofibrate, pirifibrate, ronifibrate, simfibrate, theofibrate, etc. See U.S. Pat. No. 6,384,062.

Generally, fibrates are used for conditions such as hypercholesterolemia, mixed lipidemia, hypertriglyceridemia, coronary heart disease, and peripheral vascular disease (including symptomatic carotid artery disease), and prevention of pancreatitis. Fenofibrate may also help prevent the development of pancreatitis (inflammation of the pancreas) caused by high levels of triglycerides in the blood. Fibrates are known to be useful in treating renal failure (U.S. Pat. No. 4,250,191). Fibrates may also be used for other indications where lipid regulating agents are typically used.

As used herein the term "fenofibrate" is used to mean fenofibrate (2-[4-(4-chlorobenzoyl)phenoxy]-2-methyl-propanoic acid, 1-methylethyl ester) or a salt thereof.

Fenofibrate is well known in the art and is readily recognized by one of ordinary skill. It is used to lower triglyceride (fat-like substances) levels in the blood. Specifically, fenofibrate reduces elevated LDL-C, Total-C, triglycerides, and Apo-B and increases HDL-C. The drug has also been approved as adjunctive therapy for the treatment of hypertriglyceridemia, a disorder characterized by elevated levels of very low density lipoprotein (VLDL) in the plasma.

The mechanism of action of fenofibrate has not been clearly established in man. Fenofibric acid, the active metabolite of fenofibrate, lowers plasma triglycerides apparently by inhibiting triglyceride synthesis, resulting in a reduction of VLDL released into the circulation, and also by stimulating the catabolism of triglyceride-rich lipoprotein (i.e., VLDL). Fenofibrate also reduces serum uric acid levels in hyperuricemic and normal individuals by increasing the urinary excretion of uric acid.

The absolute bioavailability of conventional microcrystalline fenofibrate cannot be determined as the compound is virtually insoluble in aqueous media suitable for injection. However, fenofibrate is well absorbed from the gastrointestinal tract. Following oral administration in healthy volunteers, approximately 60% of a single dose of conventional radiolabelled fenofibrate (i.e., TRICOR®) appeared in urine, primarily as fenofibric acid and its glucuronate conjugate, and 25% was excreted in the feces. See http://www.rxlist.com/cgi/generic3/fenofibrate_cp.htm Following oral administration, fenofibrate is rapidly hydrolyzed by esterases to the active metabolite, fenofibric acid; no unchanged fenofibrate is detected in plasma. Fenofibric acid is primarily conjugated with glucuronic acid and then excreted in urine. A small amount of fenofibric acid is reduced at the carbonyl moiety to a benzhydrol metabolite which is, in turn, conjugated with glucuronic acid and excreted in urine. Id.

2. Surface Stabilizers

The choice of a surface stabilizer for a fibrate is non-trivial and required extensive experimentation to realize a desirable formulation. Accordingly, the present invention is directed to the surprising discovery that nanoparticulate fibrate, preferably fenofibrate, compositions can be made.

Combinations of more than one surface stabilizer can be used in the invention. Useful surface stabilizers which can be employed in the invention include, but are not limited to, known organic and inorganic pharmaceutical excipients. Such excipients include various polymers, low molecular weight oligomers, natural products, and surfactants. Surface stabilizers include nonionic, anionic, cationic, ionic, and zwitterionic surfactants.

Representative examples of surface stabilizers useful in the invention include, but are not limited to, hydroxypropyl methylcellulose (now known as hypromellose), hydroxypropylcellulose, polyvinylpyrrolidone, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hypromellose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-1OG® or Surfactant 10-G® (Olin Chemicals, Stamford, Conn.); Crodestas SL40® (Croda, Inc.); and SA9OHCO, which is $C_{18}H_{37}CH_2(CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, and the like.

If desirable, the nanoparticulate fibrate, preferable fenofibrate, compositions of the invention can be formulated to be phospholipid-free.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quaternary ammonium compounds, such as stearyltrimethylammonium chloride, benzyl-di(2-chloroethyl)etbylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl(ethenoxy)$_4$ ammonium chloride or bromide, N-alkyl($C_{12-18}$)dimethylbenzyl ammonium chloride, N-alkyl($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Distearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylarnides; methylated quaternary polymers, such as poly[diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Nonpolymeric surface stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$—$R_4$ are $CH_3$;
(ii) one of $R_1$—$R_4$ is $CH_3$;
(iii) three of $R_1$—$R_4$ are $CH_3$;
(iv) all of $R_1$—$R_4$ are $CH_3$;
(v) two of $R_1$—$R_4$ are $CH_3$, one of $R_1$—$R_4$ is $C_6H_5CH_2$, and one of $R_1$—$R_4$ is an alkyl chain of seven carbon atoms or less;
(vi) two of $R_1$—$R_4$ are $CH_3$, one of $R_1$—$R_4$ is $C_6H_5CH_2$, and one of $R_1$—$R_4$ is an alkyl chain of nineteen carbon atoms or more;
(vii) two of $R_1$—$R_4$ are $CH_3$ and one of $R_1$—$R_4$ is the group $C_6H_5(CH_2)_n$, where n>1;
(viii) two of $R_1$—$R_4$ are $CH_3$, one of $R_1$—$R_4$ is $C_6H_5CH_2$, and one of $R_1$—$R_4$ comprises at least one heteroatom;
(ix) two of $R_1$—$R_4$ are $CH_3$, one of $R_1$—$R_4$ is $C_6H_5CH_2$, and one of $R_1$—$R_4$ comprises at least one halogen;
(x) two of $R_1$—$R_4$ are $CH_3$, one of $R_1$—$R_4$ is $C_6H_5CH_2$, and one of $R_1$—$R_4$ comprises at least one cyclic fragment;
(xi) two of $R_1$—$R_4$ are $CH_3$ and one of $R_1$—$R_4$ is a phenyl ring; or
(xii) two of $R_1$—$R_4$ are $CH_3$ and two of $R_1$—$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quatemium-15), distearyldimonium chloride (Quatemium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectorite, stearyl trihydroxyethyl propylenediarnine dihydrofluoride, tallowtrimonium chloride, and hexadecyltrimethyl ammonium bromide.

In one embodiment of the invention, the preferred one or more surface stabilizers of the invention is any suitable surface stabilizer as described below, with the exclusion of PEG-derivatized vitamin E, which is a non-ionic compound. In another embodiment of the invention, the preferred one or more surface stabilizers of the invention is any suitable surface stabilizer as described below, with the exclusion of phospholipids. Finally, in another embodiment of the invention, the preferred one or more surface stabilizers of the invention is any substance which is categorized by the USFDA as GRAS ("Generally Recognized As Safe").

Preferred surface stabilizers of the invention include, but are not limited to, hypromellose, docusate sodium (DOSS), Plasdone® S630 (random copolymer of vinyl pyrrolidone and vinyl acetate in a 60:40 ratio), hydroxypropyl cellulose SL (HPC-SL), sodium lauryl sulfate (SLS), and combinations thereof. Particularly preferred combinations of surface stabilizers include, but are not limited to, hypromellose and DOSS; Plasdone® S630 and DOSS; HPC-SL and DOSS; and hypromellose, DOSS, and SLS.

The surface stabilizers are commercially available and/or can be prepared by techniques known in the art. Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

3. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarnellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

4. Nanoparticulate Fibrate Particle Size

The compositions of the invention contain nanoparticulate fibrate particles, preferably nanoparticulate fenofibrate particles, which have an effective average particle size of less than about 2000 nm (i.e., 2 microns), less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

By "an effective average particle size of less than about 2000 nm" it is meant that at least 50% of the fibrate, preferably fenofibrate, particles have a particle size of less than the effective average, by weight, i.e., less than about 2000 nm, 1900 nm, 1800 nm, etc., when measured by the above-noted techniques. Preferably, at least about 70%, about 90%, or about 95% of the fibrate, preferably fenofibrate, particles have a particle size of less than the effective average, i.e., less than about 2000 nm, 1900 nm, 1800 nm, 1700 nm, etc.

In one embodiment of the invention, at least 99% of the fibrate particles ("$D_{99}$") have a particle size less than about 500 nm, less than about 450 nm, less than about 400 nm, less than about 350 nm, less than about 300 nm, less than about 250 nm, less than about 200 nm, less than about 150 nm, or less than about 100 nm. In another embodiment of the invention, at least 50% of the fibrate particles ("$D_{50}$") have a particle size less than about 350 nm, less than about 300 nm, less than about 250 nm, less than about 200 nm, less than about 150 nm, less than about 100 nm, or less than about 75 nm. In yet another embodiment of the invention, the mean particle size of the fibrate composition is less than about 100 nm, less than about 75 nm, or less than about 50 nm.

In the present invention, the value for $D_{50}$ of a nanoparticulate fibrate, preferably fenofibrate, composition is the particle size below which 50% of the fibrate particles fall, by weight. Similarly, D90 is the particle size below which 90% of the fibrate particles fall, by weight.

5. Concentration of the Fibrate and Surface Stabilizers

The relative amounts of a fibrate, preferably fenofibrate, and one or more surface stabilizers can vary widely. The optimal amount of the individual components can depend, for example, upon the particular fibrate selected, the hydrophilic lipophilic balance (HLB), melting point, and the surface tension of water solutions of the stabilizer, etc.

The concentration of the fibrate, preferably fenofibrate, can vary from about 99.5% to about 0.001%, from about 95% to about 0.1%, or from about 90% to about 0.5%, by weight, based on the total combined weight of the fibrate and at least one surface stabilizer, not including other excipients.

The concentration of the at least one surface stabilizer can vary from about 0.5% to about 99.999%, from about 5.0% to about 99.9%, or from about 10% to about 99.5%, by weight, based on the total combined dry weight of the fibrate and at least one surface stabilizer, not including other excipients.

6. Exemplary Nanoparticulate Fenofibrate Tablet Formulations

Several exemplary fenofibrate tablet formulations of the invention are given below. These examples are not intended to limit the claims in any respect, but rather provide exemplary tablet formulations of fenofibrate of the invention which can be utilized in the methods of the invention. Such exemplary tablets can also comprise a coating agent.

| Exemplary Nanoparticulate Fenofibrate Tablet Formulation #1 | |
|---|---|
| Component | g/Kg |
| Fenofibrate | about 50 to about 500 |
| Hypromellose, USP | about 10 to about 70 |
| Docusate Sodium, USP | about 1 to about 10 |
| Sucrose, NF | about 100 to about 500 |
| Sodium Lauryl Sulfate, NF | about 1 to about 40 |
| Lactose Monohydrate, NF | about 50 to about 400 |
| Silicified Microcrystalline Cellulose | about 50 to about 300 |
| Crospovidone, NF | about 20 to about 300 |
| Magnesium Stearate, NF | about 0.5 to about 5 |

Exemplary Nanoparticulate
Fenofibrate Tablet Formulation #2

| Component | g/Kg |
|---|---|
| Fenofibrate | about 100 to about 300 |
| Hypromellose, USP | about 30 to about 50 |
| Docusate Sodium, USP | about 0.5 to about 10 |
| Sucrose, NF | about 100 to about 300 |
| Sodium Lauryl Sulfate, NF | about 1 to about 30 |
| Lactose Monohydrate, NF | about 100 to about 300 |
| Silicified Microcrystalline Cellulose | about 50 to about 200 |
| Crospovidone, NF | about 50 to about 200 |
| Magnesium Stearate, NF | about 0.5 to about 5 |

Exemplary Nanoparticulate
Fenofibrate Tablet Formulation #3

| Component | g/Kg |
|---|---|
| Fenofibrate | about 200 to about 225 |
| Hypromellose, USP | about 42 to about 46 |
| Docusate Sodium, USP | about 2 to about 6 |
| Sucrose, NF | about 200 to about 225 |
| Sodium Lauryl Sulfate, NF | about 12 to about 18 |
| Lactose Monohydrate, NF | about 200 to about 205 |
| Silicified Microcrystalline Cellulose | about 130 to about 135 |
| Crospovidone, NF | about 112 to about 118 |
| Magnesium Stearate, NF | about 0.5 to about 3 |

Exemplary Nanoparticulate
Fenofibrate Tablet Formulation #4

| Component | g/Kg |
|---|---|
| Fenofibrate | about 119 to about 224 |
| Hypromellose, USP | about 42 to about 46 |
| Docusate Sodium, USP | about 2 to about 6 |
| Sucrose, NF | about 119 to about 224 |
| Sodium Lauryl Sulfate, NF | about 12 to about 18 |
| Lactose Monohydrate, NF | about 119 to about 224 |
| Silicified Microcrystalline Cellulose | about 129 to about 134 |
| Crospovidone, NF | about 112 to about 118 |
| Magnesium Stearate, NF | about 0.5 to about 3 |

D. Methods of Making Nanoparticulate Fibrate Compositions

The nanoparticulate fibrate, preferably fenofibrate, compositions can be made using, for example, milling, homogenization, or precipitation techniques. Exemplary methods of making nanoparticulate compositions are described in the '684 patent. Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

The resultant nanoparticulate fibrate, preferably fenofibrate, compositions or dispersions can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

In one embodiment of the invention, if heat is utilized during the process of making the nanoparticulate composition, the temperature is kept below the melting point of the fibrate, preferably fenofibrate.

1. Milling to Obtain Nanoparticulate Fibrate Dispersions

Milling a fibrate, preferably fenofibrate, to obtain a nanoparticulate dispersion comprises dispersing the fibrate particles in a liquid dispersion medium in which the fibrate is poorly soluble, followed by applying mechanical means in the presence of grinding media to reduce the particle size of the fibrate to the desired effective average particle size. The dispersion medium can be, for example, water, safflower oil, ethanol, t-butanol, glycerin, polyethylene glycol (PEG), hexane, or glycol. A preferred dispersion medium is water.

The fibrate, preferably fenofibrate, particles can be reduced in size in the presence of at least one surface stabilizer. Alternatively, the fibrate particles can be contacted with one or more surface stabilizers after attrition. Other compounds, such as a diluent, can be added to the fibrate/surface stabilizer composition during the size reduction process. Dispersions can be manufactured continuously or in a batch mode.

In one embodiment of the invention, a mixture of a fibrate and one or more surface stabilizers is heated during the milling process. If a polymeric surface stabilizer is utilized, the temperature is raised to above the cloud point of the polymeric surface stabilizer but below the actual or depressed melting point of the fibrate. The utilization of heat may be important for scale up of the milling process, as it can aid in the solubilization of the one or more active agents.

2. Precipitation to Obtain Nanoparticulate Fibrate Compositions

Another method of forming the desired nanoparticulate fibrate, preferably fenofibrate, composition is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving a fibrate in a suitable solvent; (2) adding the formulation from step (1) to a solution comprising at least one surface stabilizer; and (3) precipitating the formulation from step (2) using an appropriate non-solvent. The method can be followed by removal of any formed salt, if present, by dialysis or diafiltration and concentration of the dispersion by conventional means.

3. Homogenization to Obtain Nanoparticulate Fibrate Compositions

Exemplary homogenization methods of preparing active agent nanoparticulate compositions are described in U.S. Pat. No. 5,510,118, for "Process of Preparing Therapeutic Compositions Containing Nanoparticles." Such a method comprises dispersing particles of a fibrate, preferably fenofibrate, in a liquid dispersion medium, followed by subjecting the dispersion to homogenization to reduce the particle size of the fibrate to the desired effective average particle size. The fibrate particles can be reduced in size in the presence of at least one surface stabilizer. Alternatively, the fibrate particles can be contacted with one or more surface stabilizers either before or after attrition. Other compounds, such as a diluent, can be added to the fenofibrate/surface stabilizer composition either before, during, or after the size reduction process. Dispersions can be manufactured continuously or in a batch mode.

D. Methods of Using the Fibrate Compositions of the Invention

The invention provides a method of rapidly increasing the plasma levels of a fibrate, preferably fenofibrate, in a subject. Such a method comprises orally administering to a subject an effective amount of a composition comprising a fibrate, preferably fenofibrate. The fibrate composition, when tested in fasting subjects in accordance with standard pharmacokinetic practice, produces a maximum blood plasma concentration profile in less than about 6 hours, less than about 5 hours, less than about 4 hours, less than about 3 hours, less than about 2 hours, less than about 1 hour, or less than about 30 minutes after the initial dose of the composition.

The compositions of the invention are useful in treating conditions such as hypercholesterolemia, hypertriglyceridemia, cardiovascular disorders, coronary heart disease, and peripheral vascular disease (including symptomatic carotid artery disease). The compositions of the invention can be used as adjunctive therapy to diet for the reduction of LDL-C, total-C, triglycerides, and Apo B in adult patients with primary hypercholesterolemia or mixed dyslipidemia (Fredrickson Types IIa and IIb). The compositions can also be used as adjunctive therapy to diet for treatment of adult patients with hypertriglyceridemia (Fredrickson Types IV and V hyperlipidemia). Markedly elevated levels of serum tryglycerides (e.g., >2000 mg/dL) may increase the risk of developing pancreatitis. The compositions of the invention can also be used for other indications where lipid regulating agents are typically used.

The fenofibrate compositions of the invention can be administered to a subject via any conventional means including, but not limited to, orally, rectally, ocularly, parenterally (e.g., intravenous, intramuscular, or subcutaneous), intracisternally, pulmonary, intravaginally, intraperitoneally, locally (e.g., powders, ointments or drops), or as a buccal or nasal spray. As used herein, the term "subject" is used to mean an animal, preferably a mammal, including a human or non-human. The terms patient and subject may be used interchangeably.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles including water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate fibrate, preferably fenofibrate, compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include, but are not limited to, capsules, tablets, pills, powders, and granules. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof For capsules, tablets, and pills, the dosage forms may also comprise buffering agents.

Liquid dosage forms for oral administration include pharmaceutically acceptable emulsions, solutions, suspensions, syrups, and elixirs. In addition to the fibrate, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

"Therapeutically effective amount" as used herein with respect to a fibrate, preferably a fenofibrate, dosage shall mean that dosage that provides the specific pharmacological response for which the fibrate is administered in a significant number of subjects in need of such treatment. It is emphasized that "therapeutically effective amount," administered to a particular subject in a particular instance may not be effective for 100% of patients treated for a specific disease, and will not always be effective in treating the diseases described herein, even though such dosage is deemed a "therapeutically effective amount" by those skilled in the art. It is to be further understood that fibrate dosages are, in particular instances, measured as oral dosages, or with reference to drug levels as measured in blood.

One of ordinary skill will appreciate that effective amounts of a fibrate, such as fenofibrate, can be determined empirically and can be employed in pure form or, where such forms exist, in pharmaceutically acceptable salt, ester, or prodrug form. Actual dosage levels of a fibrate, such as fenofibrate, in the nanoparticulate compositions of the invention may be varied to obtain an amount of the fibrate that is effective to obtain a desired therapeutic response for a particular composition and method of administration. The selected dosage level therefore depends upon the desired therapeutic effect, the route of administration, the potency of the administered fibrate, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

Several of the formulations in the examples that follow were investigated using a light microscope. Here, "stable" nanoparticulate dispersions (uniform Brownian motion) were readily distinguishable from "aggregated" dispersions (relatively large, nonuniform particles without motion).

TABLE 1

Nanoparticulate Fenofibrate Formulations Milled Under High Energy Conditions

| Formulation | Drug | Surface Stabilizer | Particle Size |
|---|---|---|---|
| 1 | 5% (w/w) | 1% hypromellose and 0.05% DOSS | Mean: 139 nm 90% < 266 nm |
| 2 | 5% (w/w) | 1% S630 and 0.05% DOSS | Mean: 233 nm 90% < 355 nm |

Next, the stability of the two formulations was tested in various simulated biological fluids (Table 2) and in water (Table 3) over an extended period of time. For tests in various simulated biological fluids, the composition was deemed stable if the particles remained in a dispersion format with no visible size increase or agglomeration after 30 min. incubation at 40° C. Testing in fluids representing electrolyte fluids is useful as such fluids are representative of physiological conditions found in the human body.

TABLE 2

Stability Testing of Nanoparticulate Fenofibrate Formulations 1 and 2 in Simulated Biological Fluids

| Formulation | Electrolyte Test Media #1 | Electrolyte Test Media #2 | Electrolyte Test Media #3 |
|---|---|---|---|
| 1 | Slight Agglomeration | Acceptable | Acceptable |
| 2 | Heavy Agglomeration | Acceptable | Slight Agglomeration |

TABLE 3

Stability Testing of Nanoparticulate Fenofibrate Formulations 1 and 2 in Water at 2-8° C.

| Formulation | 3 Days | 1 Week | 2 Weeks | 7 Months |
|---|---|---|---|---|
| 1 | Mean: 149 nm 90% < 289 nm | Mean: 146 nm 90% < 280 nm | Mean: 295 nm 90% < 386 nm | Mean: 1179 nm 90% < 2744 nm |
| 2 | Mean: 824 nm 90% < 1357 nm | Mean: 927 nm 90% < 1476 nm | Mean: 973 nm 90% < 1526 nm | Mean: 1099 nm 90% < 1681 nm |

EXAMPLE 1

The purpose of this example was to prepare nanoparticulate dispersions of fenofibrate, and to test the prepared compositions for stability in water and in various simulated biological fluids.

Two formulations of fenofibrate were milled, as described in Table 1, by milling the components of the compositions under high energy milling conditions in a DYNO®-Mill KDL (Willy A. Bachofen A G, Maschinenfabrik, Basle, Switzerland) for ninety minutes.

Formulation 1 comprised 5% (w/w) fenofibrate, 1% (w/w) hypromellose, and 0.05% (w/w) dioctyl sodium sulfosuccinate (DOSS), and Formulation 2 comprised 5% (w/w) fenofibrate, 1% (w/w) Pluronic® S-630 (a random copolymer of vinyl acetate and vinyl pyrrotidone), and 0.05% (w/w) DOSS. The particle size of the resultant compositions was measured using a Horiba LA-910 Laser Scattering Particle Size Distribution Analyzer ((Horiba Instrumnents, Irvine, Calif.).

Stability results indicate that Formulation 1 is preferred over Formulation 2, as Formulation 2 exhibited slight agglomeration in simulated intestinal fluid and unacceptable particle size growth over time.

EXAMPLE 2

The purpose of this example was to prepare nanoparticulate dispersions of fenofibrate, followed by testing the stability of the compositions in various simulated biological fluids.

Four formulations of fenofibrate were prepared, as described in Table 4, by milling the components of the compositions in a DYNO®-Mill KDL (Willy A. Bachofen A G, Maschinenfabrik, Basle, Switzerland) for ninety minutes.

Formulation 3 comprised 5% (w/w) fenofibrate, 1% (w/w) hydroxypropylcellulose SL (HPC-SL), and 0.01% (w/w) DOSS; Formulation 4 comprised 5% (w/w) fenofibrate, 1% (w/w) hypromellose, and 0.01% (w/w) DOSS; Formulation 5 comprised 5% (w/w) fenofibrate, 1% (w/w)

polyvinylpyrrolidone (PVP K29/32), and 0.01% (w/w) DOSS; and Formulation 6 comprised 5% (w/w) fenofibrate, 1% (w/w) Pluronic® S-630, and 0.01% (w/w) DOSS.

The particle size of the resultant compositions was measured using a Horiba LA-910 Laser Scattering Particle Size Distribution Analyzer ((Horiba Instruments, Irvine, Calif.).

TABLE 4

Particle Size of Nanoparticulate Fenofibrate Formulations

| Formulation | Drug | Surface Stabilizer | Particle Size |
|---|---|---|---|
| 3 | 5% (w/w) | 1% HPC-SL and 0.01% DOSS | Mean: 696 nm 90% < 2086 nm |
| 4 | 5% (w/w) | 1% hypromellose and 0.01% DOSS | Mean: 412 nm 90% < 502 nm |
| 5 | 5% (w/w) | 1% PVP and 0.01% DOSS | Mean: 4120 nm 90% < 9162 nm |
| 6 | 5% (w/w) | 1% S630 and 0.01% DOSS | Mean: 750 nm 90% < 2184 nm |

The results indicate that PVP is not a satisfactory surface stabilizer for fenofibrate, at the particular concentrations of fenofibrate and PVP disclosed, in combination with DOSS, as the mean particle size of Formulation 5 was over two microns. However, PVP may be useful as a surface stabilizer for fenofibrate when it is used alone, in combination with another surface stabilizer, or when different concentrations of PVP and/or fenofibrate are utilized.

Next, the stability of Formulations 4 and 6 was tested in various simulated biological fluids (Table 5).

TABLE 5

Stability Testing of Nanoparticulate Fenofibrate Formulations 3-6 in Simulated Biological Fluids

| Formulation | Electrolyte Test Media #1 | Electrolyte Test Media #2 | Electrolyte Test Media #3 |
|---|---|---|---|
| 3 | N/A | N/A | N/A |
| 4 | Acceptable | Acceptable | Acceptable |
| 5 | N/A | N/A | N/A |
| 6 | Agglomeration | Very slight agglomeration | Slight agglomeration |

The results indicate that Formulation 4, comprising hypromellose and DOSS as surface stabilizers, is preferred as the initial particle size is within the useable range (i.e., 90%<512 nm) and the composition shows no aggregation in various simulated biological fluids.

The next set of examples relate to the redispersibility of the spray granulated powders of the nanoparticulate fenofibrate compositions. The purpose for establishing redispersibility of the spray granulated powder is to determine whether the solid nanoparticulate fenofibrate composition of the invention will redisperse when introduced into in vitro or in vivo biologically relevant media.

EXAMPLE 3

The purpose of this example was to evaluate the redispersibility of spray granulated powders of preferred nanoparticulate fenofibrate compositions comprising hypromellose and DOSS with or without SLS, a preferred small anionic surfactant.

The redispersibility of two powder forms of a spray granulated powder of nanoparticulate fenofibrate was determined, the results of which are shown in Table 6.

TABLE 6

| Physical form | Powder | Powder |
|---|---|---|
| Drug:Sucrose | 1:0.6 | 1:1 |
| Hypromellose:DOSS | 1:0.2 | — |
| Hypromellose:DOSS + SLS | — | 1:0.3 |
| Redispersibility DI water | | |
| Mean (nm) | 390 | 182 |
| D90 (nm) | 418 | 260 |
| % < 1000 nm | 95.9 | 100.0 |
| Electrolyte Test Media #2 | | |
| Mean (nm) | 258 | 193 |
| D90 (nm) | 374 | 276 |
| % < 1000 nm | 99.7 | 100.0 |
| Electrolyte Test Media #3 | | |
| Mean (nm) | 287 | 225 |
| D90 (nm) | 430 | 315 |
| % < 1000 nm | 99.6 | 100.0 |

The results show that powders prepared from a granulation feed dispersion having hypromellose, DOSS and SLS exhibit excellent redispersiblity.

EXAMPLE 4

The purpose of this example was to test the redispersibility of a spray granulated powder of nanoparticulate fenofibrate comprising higher levels of DOSS and SLS, as compared to Example 3. The results are shown in Table 7.

TABLE 7

| Physical form | Powder |
|---|---|
| Drug:Sucrose | 1:1 |
| Hypromellose:SLS + DOSS | 1:0.45 |
| Redispersibility DI water | |
| Mean (nm) | 196 |
| D90 (nm) | 280 |
| % <1000 nm | 100 |
| Electrolyte Test Media #2 | |
| Mean (nm) | 222 |
| D90 (nm) | 306 |
| % <1000 nm | 100 |
| Electrolyte Test Media #3 | |
| Mean (nm) | 258 |
| D90 (nm) | 362 |
| % <1000 nm | 100 |

Excellent redispersibility was observed for all of the tested compositions in simulated biological fluids.

EXAMPLE 5

The purpose of this example was to prepare a nanoparticulate fenofibrate tablet formulation.

A fenofibrate nanoparticulate dispersion was prepared by combining the materials listed in Table 8, followed by milling the mixture in a Netzsch LMZ2 Media Mill with Grinding Chamber with a flow rate of 1.0±0.2 LPM and an agitator speed of 3000±100 RPM, utilizing Dow PolyMill™ 500 micron milling media. The resultant mean particle size of the nanoparticulate fenofibrate dispersion (NCD), as measured by a Horiba LA-910 Laser Scattering Particle Size Distribution Analyzer ((Horiba Instruments, Irvine, Calif.) was 169 nm.

TABLE 8

Nanoparticulate Fenofibrate Dispersion

| Fenofibrate | 300 g/Kg |
|---|---|
| Hypromellose, USP (Pharmacoat ® 603) | 60 g/Kg |
| Docusate Sodium, USP | 0.75 g/Kg |
| Purified Water | 639.25 g/Kg |

Next, a granulated feed dispersion (GFD) was prepared by combining the nanoparticulate fenofibrate dispersion with the additional components specified in Table 9.

TABLE 9

Nanoparticulate Fenofibrate Granular Feed Dispersion

| Nanoparticulate Fenofibrate Dispersion | 1833.2 g |
|---|---|
| Sucrose, NF | 550.0 g |
| Sodium Lauryl Sulfate, NF | 38.5 g |
| Docusate Sodium, USP/EP | 9.6 g |
| Purified Water | 723.2 g |

The fenofibrate GFD was sprayed onto lactose monohydrate (500 g) to form a spray granulated intermediate (SGI) using a Vector Multi-1 Fluid Bed System set to run at the parameters specified in Table 10, below.

TABLE 10

Fluid Bed System Parameters

| Inlet Air Temperature | 70 ± 10° C. |
|---|---|
| Exhaust/Product Air Temperature | 37 ± 5° C. |
| Air Volume | 30 ± 20 CFM |
| Spray Rate | 15 ± 10 g/min |

The resultant spray granulated intermediate (SGI) of the nanoparticulate fenofibrate is detailed in Table 11, below.

TABLE 11

Spray Granulated Intermediate of the Nanoparticulate Fenofibrate

| Fenofibrate NCD | 1833.2 g |
|---|---|
| Sucrose, NF | 550.0 g |
| Sodium Lauryl Sulfate, NF | 38.5 g |
| Docusate Sodium, USP/EP | 9.6 g |
| Lactose Monohydrate, NF | 500 g |

The nanoparticulate fenofibrate SGI was then tableted using a Kilian tablet press with a 0.700×0.300" plain upper and lower caplet shape punches. Each tablet has 160 mg of fenofibrate. The resulting tablet formulation is shown below in Table 12.

TABLE 12

Nanoparticulate Fenofibrate Tablet Formulation

| Nanoparticulate Fenofibrate Spray Granulated Intermediate | 511.0 mg |
|---|---|
| Silicified Microcrystalline Cellulose | 95.0 mg |
| Crospovidone, NF | 83.0 mg |
| Magnesium Stearate, NF | 1.0 mg |

EXAMPLE 6

The purpose of this example was to assess the effect of food on the bioavailability of a nanoparticulate fenofibrate tablet formulation, as prepared in Example 5.

Study Design

A single dose, three way cross-over design study, with eighteen subjects, was conducted. The three treatments consisted of:

Treatment A: 160 mg nanoparticulate fenofibrate tablet administered under fasted conditions;

Treatment B: 160 mg nanoparticulate fenofibrate tablet administered under high fat fed conditions; and Treatment C: 200 mg micronized fenofibrate capsule (TRICOR®) administered under low fat fed conditions.

"Low fat fed" conditions are defined as 30% fat—400 Kcal, and "high fat fed" conditions are defined as 50% fat—1000 Kcal. The length of time between doses in the study was 10 days.

Results

Figure 2:
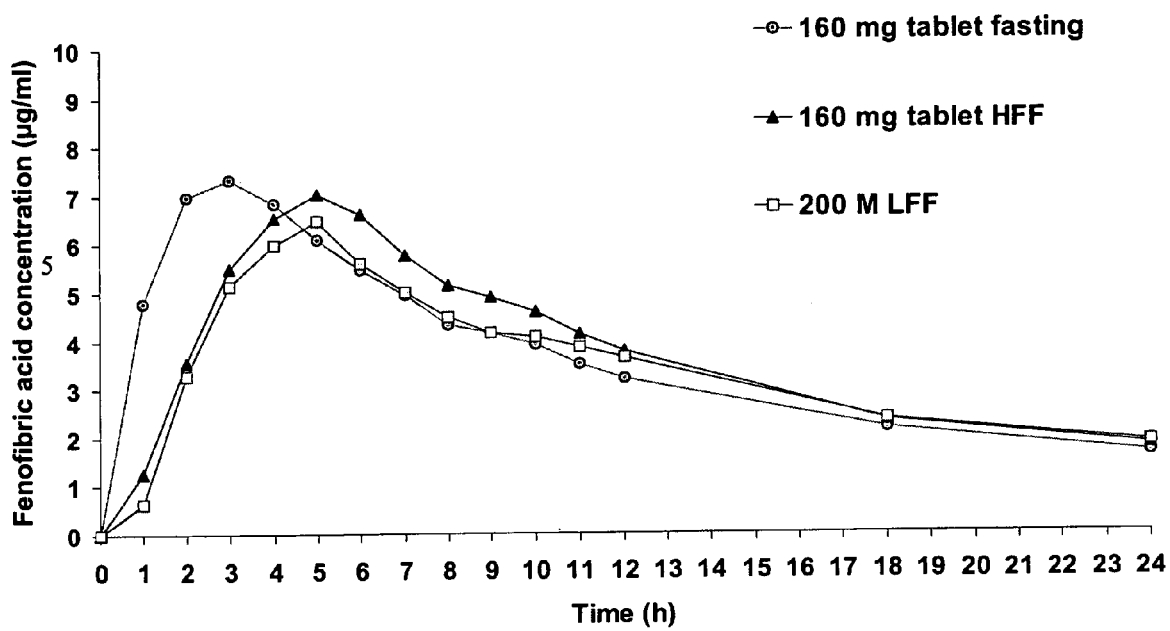
FIG. 2: Shows the fenofibric acid concentration (μg/ml) over a period of 24 hours for a single dose of: (a) a 160 mg nanoparticulate fenofibrate tablet administered to a fasting subject; (b) a 160 mg nanoparticulate fenofibrate tablet administered to a high fat fed subject; and (c) a 200 mg microcrystalline (TRICOR®) capsule administered to a low fat fed subject.

FIG. 1 shows the plasma fenofibric acid profiles (i.e., the fenofibric acid concentration (µg/ml)) over a period of 120 hours for Treatment A, Treatment B, and Treatment C. FIG. 2 shows the same fenofibric acid profiles, but over a 24 hour period rather than a 120 hour period.

Surprisingly, all three Treatments produce approximately the same profile, although the nanoparticulate fenofibrate tablet administered under fasting conditions exhibited a marginally higher maximum fenofibrate concentration. These results are significant for several reasons. First, the nanoparticulate fenofibrate tablet is effective at a lower dosage than that of the conventional microcrystalline fenofibrate capsule: 160 mg vs. 200 mg. A lower dosage is always seen as beneficial for the patient, as less active agent is administered to the patient.

Second, the results show that the nanoparticulate fenofibrate tablet formulation does not exhibit significant differences in absorption when administered in the fed versus the fasted state. This is significant as it eliminates the need for a patient to ensure that they are taking a dose with or without food. Therefore, the nanoparticulate fenofibrate dosage form will result in increased patient compliance. With poor patient compliance an increase in cardiovascular problems or other conditions for which the fenofibrate is being prescribed can result.

The pharmacokinetic parameters of the three tests are shown below in Table 13.

TABLE 13

| | Pharmacokinetic Parameters (Mean, Standard Deviation, CV %) | | |
|---|---|---|---|
| | Treatment A | Treatment B | Treatment C |
| AUC (µg/mL · h) | mean = 139.41 | mean = 138.55 | mean = 142.96 |
| | SD = 45.04 | SD = 41.53 | SD = 51.28 |
| | CV % = 32% | CV % = 30% | CV % = 36% |
| $C_{max}$ (µg/mL) | mean = 8.30 | mean = 7.88 | mean = 7.08 |
| | SD = 1.37 | SD = 1.74 | SD = 1.72 |
| | CV % = 17% | CV % = 22% | CV % = 24% |

The pharmacokinetic parameters first demonstrate that there is no difference in the amount of drug absorbed when the nanoparticulate fenofibrate tablet is administered in the fed versus the fasted condition (see the AUC results; 139.41 µg/mL.h for the dosage form administered under fasted conditions and 138.55 µg/mL.h for the dosage form administered under fed conditions). Second, the data show that there was no difference in the rate of drug absorption when the nanoparticulate fenofibrate tablet is administered in the fed versus the fasted condition (see the $C_{max}$ results; 8.30 µg/mL for the dosage form administered under fasted conditions and 7.88 µg/mL for the dosage form administered under fed conditions). Thus, the nanoparticulate fenofibrate dosage form eliminates the effect of food on the pharmacokinetics of fenofibrate. Accordingly, the invention encompasses a fibrate composition wherein the pharmacokinetic profile of the fibrate is not affected by the fed or fasted state of a subject ingesting the composition.

Bioequivalence of the Nanoparticulate Fenofibrate Dosage Form When Administered in the Fed vs Fasted State Using the data from Table 13, it was determined whether administration of a nanoparticulate fenofibrate tablet in a fasted state was bioequivalent to administration of a nanoparticulate fenofibrate tablet in a fed state, pursuant to regulatory guidelines. The relevant date from Table 13 is shown below in Table 14, along with the 90% Confidence Intervals (CI). Under U.S. FDA guidelines, two products or methods are bioequivalent if the 90% CI for AUC and $C_{max}$ are between 0.80 to 1.25. As shown below in Table 14, the 90% CI ratio for the nanoparticulate fenofibrate fed/fasted methods is 0.952:1.043 for AUC and 0.858:1.031 for $C_{max}$.

TABLE 14

Bioequivalence of Nanoparticulate Fenofibrate Tablet HFF vs. Nanoparticulate Fenofibrate Tablet Fasted

|  |  |  | CI 90% on log-transformed data |
|---|---|---|---|
| AUC (µg/mL · h) | Nanoparticulate Fenofibrate Tablet 160 mg HFF | 139 | 0.952:1.043 |
|  | Nanoparticulate Fenofibrate Tablet 160 mg Fasted | 139 |  |
| Cmax (µg/mL) | Nanoparticulate Fenofibrate Tablet 160 mg HFF | 7.88 | 0.858:1.031 |
|  | Nanoparticulate Fenofibrate Tablet 160 mg Fasted | 8.30 |  |

Accordingly, pursuant to regulatory guidelines, administration of a nanoparticulate fenofibrate tablet in a fasted state is bioequivalent to administration of a nanoparticulate fenofibrate tablet in a fed state. Thus, the invention encompasses a fibrate composition wherein administration of the composition to a subject in a fasted state is bioequivalent to administration of the composition to a subject in a fed state.

Moreover, as shown by the data in Table 15 below, administration of a 160 mg nanoparticulate fenofibrate tablet in a fed state is bioequivalent to administration of a 200 mg conventional microcrystalline fenofibrate capsule (TRICOR®) in a fed state. This is because CI 90% for the two treatments is within 0.80 to 1.25 for AUC and $C_{max}$.

TABLE 15

Bioequivalence of Nanoparticulate 160 mg Fenofibrate Tablet HFF vs. a Microcrystalline 200 mg Fenofibrate Capsule (TRICOR ®) LFF

|  |  |  | CI 90% on log-transformed data |
|---|---|---|---|
| AUC (µg/mL · h) | Nanoparticulate 160 mg Fenofibrate Tablet HFF | 139 | 0.936:1.026 |

TABLE 15-continued

Bioequivalence of Nanoparticulate 160 mg Fenofibrate Tablet HFF vs. a Microcrystalline 200 mg Fenofibrate Capsule (TRICOR ®) LFF

|  |  |  | CI 90% on log-transformed data |
|---|---|---|---|
|  | Microcrystalline 200 mg Fenofibrate Capsule (TRICOR ®) LFF | 143 |  |
| Cmax (µg/mL) | Nanoparticulate 160 mg Fenofibrate Tablet HFF | 7.88 | 1.020:1.226 |
|  | Microcrystalline 200 mg Fenofibrate Capsule (TRICOR ®) LFF | 7.08 |  |

Finally, as shown by the data in Table 16, below, administration of a 160 mg nanoparticulate fenofibrate tablet in a fasted state is not bioequivalent to administration of a 200 mg conventional microcrystalline fenofibrate capsule (TRICOR®) in a fed state. This is because CI 90% for the two treatments is outside 0.80 to 1.25 for AUC and $C_{max}$.

TABLE 16

Non-Bioequivalence of Nanoparticulate 160 mg Fenofibrate Tablet Fasted vs. a Microcrystalline 200 mg Fenofibrate Capsule (TRICOR ®) LFF

|  |  |  | CI 90% on log-transformed data |
|---|---|---|---|
| AUC (µg/mL · h) | Nanoparticulate 160 mg Fenofibrate Tablet Fasted | 139 | 0.939:1.030 |
|  | Microcrystalline 200 mg Fenofibrate Capsule (TRICOR ®) LFF | 143 |  |
| Cmax (µg/mL) | Nanoparticulate 160 mg Fenofibrate Tablet Fasted | 8.30 | 1.084:1.304 |
|  | Microcrystalline 200 mg Fenofibrate Capsule (TRICOR ®) LFF | 7.08 |  |

The non-bioequivalence is significant, because it means that the nanoparticulate fenofibrate dosage form exhibits significantly greater drug absorption. For the nanoparticulate fenofibrate dosage form to be bioequivalent to the conventional microcrystalline fenofibrate dosage form (e.g., TRICOR®), the dosage form would have to contain significantly less drug. Thus, the nanoparticulate fenofibrate dosage form significantly increases the bioavailability of the drug.

EXAMPLE 7

The purpose of this example was to provide nanoparticulate fenofibrate tablet formulations prepared as described in Example 5, above.

Shown below in Table 17 is the nanoparticulate fenofibrate dispersion used for making the nanoparticulate fenofibrate tablet formulations.

TABLE 17

| Nanoparticulate Fenofibrate Dispersion | |
|---|---|
| Fenofibrate | 194.0 g/Kg |
| Hypromellose, USP (Pharmacoat ® 603) | 38.81 g/Kg |
| Docusate Sodium, USP | 0.485 g/Kg |

TABLE 17-continued

Nanoparticulate Fenofibrate Dispersion

| Water for injection, USP, EP | 572.7 g/Kg |
|---|---|
| Sucrose, NF | 194.0 g/Kg |
| Actual Total | 1000.0 |

Two different tablets were made using the dispersion: a 145 mg nanoparticulate fenofibrate tablet and a 48 mg nanoparticulate fenofibrate table.

A granulated feed dispersion (GFD) was prepared by combining the nanoparticulate fenofibrate dispersion with sucrose, docusate sodium, and sodium lauryl sulfate.

The fenofibrate GFD was processed and dried in a fluid-bed column (Vector Multi-1 Fluid Bed System), along with lactose monohydrate. The resultant spray granulated intermediate (SGI) was processed through a cone mill, followed by (1) processing in a bin blender with silicified microcrystalline cellulose and crospovidone, and (2) processing in a bin blender with magnesium stearate. The resultant powder was tableted in a rotary tablet press, followed by coating with Opadry® AMB using a pan coater.

Table 18 provides the composition of the 145 mg fenofibrate tablet, and Table 19 provides the composition of the 48 mg fenofibrate tablet.

TABLE 18

145 mg Nanoparticulate Fenofibrate Tablet Formulation

| Component | g/Kg |
|---|---|
| Fenofibrate | 222.54 |
| Hypromellose, USP | 44.506 |
| Docusate Sodium, USP | 4.4378 |
| Sucrose, NF | 222.54 |
| Sodium Lauryl Sulfate, NF | 15.585 |
| Lactose Monohydrate, NF | 202.62 |
| Silicified Microcrystalline Cellulose | 132.03 |
| Crospovidone, NF | 115.89 |
| Magnesium Stearate, NF | 1.3936 |
| Opadry OY-28920 | 38.462 |
| Actual Total | 1000.0 |

TABLE 19

48 mg Nanoparticulate Fenofibrate Tablet Formulation

| Component | g/Kg |
|---|---|
| Fenofibrate | 221.05 |
| Hypromellose, USP | 44.209 |
| Docusate Sodium, USP | 4.4082 |
| Sucrose, NF | 221.05 |
| Sodium Lauryl Sulfate, NF | 15.481 |
| Lactose Monohydrate, NF | 201.27 |
| Silicified Microcrystalline Cellulose | 131.14 |
| Crospovidone, NF | 115.12 |
| Magnesium Stearate, NF | 1.3843 |
| Opadry OY-28920 | 44.890 |
| Actual Total | 1000.0 |

EXAMPLE 8

The purpose of this example was to compare the dissolution of a nanoparticulate 145 mg fenofibrate dosage form according to the invention with a conventional microcrystalline form of fenofibrate (TRICOR®) in a dissolution medium which is representative of in vivo conditions.

The dissolution of the 145 mg nanoparticulate fenofibrate tablet, prepared in Example 7, was tested in a dissolution medium which is discriminating. Such a dissolution medium will produce two very different dissolution curves for two products having very different dissolution profiles in gastric juices; i.e., the dissolution medium is predictive of in vivo dissolution of a composition.

The dissolution medium employed was an aqueous medium containing the surfactant sodium lauryl sulfate at 0.025 M. Determination of the amount dissolved was carried out by spectrophotometry, and the tests were repeated 12 times. The rotating blade method (European Pharmacopoeia) was used under the following conditions:

volume of media: 1000 ml;
media temperature: 37 ° C.;
blade rotation speed: 75 RPM;
samples taken: every 2.5 minutes;

The results are shown below in Table 20. The table shows the amount (%) of the solid dosage form dissolved at 5, 10, 20, and 30 minutes for twelve different samples, as well as the mean (%) and standard deviation (%) results.

TABLE 20

Dissolution Profile of the Nanoparticulate Fenofibrate 145 mg Table

| Test Sample | 5 min. | 10 min. | 20 min. | 30 min. |
|---|---|---|---|---|
| 1 | 36.1 | 80.9 | 101.7 | 103.6 |
| 2 | 73.4 | 100.5 | 100.1 | 101.8 |
| 3 | 44.0 | 85.6 | 100.0 | 101.4 |
| 4 | 41.0 | 96.1 | 102.3 | 102.5 |
| 5 | 58.7 | 92.9 | 103.4 | 103.5 |
| 6 | 51.9 | 97.8 | 102.6 | 103.4 |
| 7 | 28.6 | 66.9 | 99.3 | 100.4 |
| 8 | 44.7 | 97.4 | 98.8 | 99.3 |
| 9 | 30.1 | 76.9 | 97.0 | 98.0 |
| 10 | 33.6 | 76.8 | 101.8 | 103.5 |
| 11 | 23.5 | 52.6 | 95.8 | 104.0 |
| 12 | 34.6 | 66.9 | 102.8 | 102.2 |
| Mean (%) | 41.7 | 82.6 | 100.5 | 102.0 |
| Standard Deviation (%) | 14.1 | 15.2 | 2.4 | 1.9 |

U.S. Pat. No. 6,277,405, for "Fenofibrate Pharmaceutical Composition Having High Bioavailability and Method for Preparing It," describes dissolution of a conventional microcrystalline 160 mg fenofibrate dosage form, e.g. TRICOR®, using the same method described above for the nanoparticulate fenofibrate dosage form (Example 2, cols. 8-9). The results show that the conventional fenofibrate dosage form has a dissolution profile of 10% in 5 min., 20% in 10 min., 50% in 20 min., and 75% in 30 min.

The results show that the nanoparticulate fenofibrate dosage form had dramatically more rapid dissolution as compared to the conventional microcrystalline form of fenofibrate. For example, while within 5 minutes approximately 41.7% of the nanoparticulate fenofibrate dosage form had dissolved, only 10% of the TRICOR® dosage form had dissolved. Similarly, while at 10 min. about 82.6% of the nanoparticulate fenofibrate dosage form was dissolved, only about 20% of the TRICOR® dosage form had dissolved during the same time period. Finally, while at 30 min. basically 100% of the nanoparticulate dosage form had dissolved, only about 75% of the conventional fenofibrate dosage form had dissolved during the same time period.

Thus, the nanoparticulate fenofibrate dosage forms of the invention exhibit dramatically improved rates of dissolution.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A stable fenofibrate composition for oral administration comprising:
   (a) particles of fenofibrate having a D50 particle size of less than about 500 nm, and
   (b) at least one surface stabilizer,
   wherein:
      (i) the composition exhibits bioequivalence upon administration to a human subject in a fed state as compared to administration to a human subject in a fasted state; where bioequivalency is established by:
         (a) a 90% Confidence Interval for AUC which is between 80% and 125%, and
         (b) a 90% Confidence Interval for $C_{max}$, which is between 80% and 125%;
      (ii) the composition redisperses in a biorelevant media; and
      (iii) the composition is phospholipid-free.

2. The composition of claim 1, which is bioequivalent to a micronized 54 mg fenofibrate oral solid dosage form.

3. The composition of claim 1, which is bioequivalent to a micronized 160 mg fenofibrate oral solid dosage form.

4. The composition of claim 3, which is a single daily dose.

5. The composition of claim 1, which is bioequivalent to a micronized 200 mg fenofibrate oral solid dosage form.

6. The composition of claim 5, which is a single daily dose.

7. The composition of claim 1, wherein the difference in AUC of the fenofibrate composition, when administered to a human subject in the fed versus the fasted state, is selected from the group consisting of less than about 35%, less than about 30%, less than about 25%, less than about 20%, less than about 15%, less than about 10%, less than about 5%, and less than about 3%.

8. The composition of claim 1, which when administered to a human subject at a dose of about 160 mg presents an AUC of about 139 µg/mL.h.

9. The composition of claim 1 which exhibits a $T_{max}$ after administration to fasting human subjects selected from the group consisting of less than about 6 hours, less than about 5 hours, less than about 4 hours, less than about 3 hours, less than about 2 hours, less than about 1 hour, and less than about 30 minutes.

10. The composition of claim 1, wherein in comparative pharmacokinetic testing with a 160 mg micronized fenofibrate tablet or 200 mg micronized fenofibate capsule, which are standard commercial formulations of microcrystalline fenofibrate, the composition of claim 136 exhibits a $T_{max}$ selected from the group consisting of less than about 90%, less than about 80%, less than about 70%, less than about 50%, less than about 30%, and less than about 25% of the $T_{max}$ exhibited by the micronized fenofibate tablet or capsule.

11. The composition of claim 1, wherein the fenofibrate is present in an amount selected from the group consisting of:
   (a) about 50 to about 500 g of fenofibrate per kg of composition;
   (b) about 100 to about 300 g of fenofibrate per kg of composition;
   (c) about 200 to about 225 g of fenofibrate per kg of composition; and
   (d) about 119 to about 224 g of fenofibrate per kg of composition.

12. The composition of claim 1 comprising a dosage of about 145 mg of fenofibrate, wherein:
   (a) the dosage is therapeutically effective; and
   (b) the composition is bioequivalent to a 160 mg micronized fenofibate tablet or 200 mg micronized fenofibate capsule, wherein bioequivalency, when administered to a human, is established by a 90% Confidence Interval of between 0.80 and 1.25 for both $C_{max}$ and AUC.

13. The composition of claim 1 comprising a dosage of about 48 mg of fenofibrate, wherein:
   (a) the dosage is therapeutically effective; and
   (b) the composition is bioequivalent to a 54 mg micronized fenofibate tablet, wherein biocquivalency, when administered to a human, is established by a 90% Confidence Interval of between 0.80 and 1.25 for both $C_{max}$ and AUC.

14. The composition of claim 1 comprising a dosage of about 160 mg of fenofibrate, wherein following administration to fasting human subjects the blood levels of fenofibric acid are at least 4.5 µg/mL at one hour.

15. The composition of claim 1 comprising a dosage of about 160 mg of fenofibrate, wherein following administration to fasting human subjects the blood levels of fenofibric acid are at least 6.5 g/mL at two hours.

16. The composition of claim 1 comprising a dosage of about 160 mg of fenofibrate, wherein following administration to fasting human subjects the blood levels of fenofibric acid are at least 7.0 µg/mL at three hours.

17. The composition of claim 1 comprising a dosage of about 160 mg of fenofibrate, wherein following administration to fasting human subjects the blood levels of fenofibric acid are at least 1.5 µg/mL at twenty-four hours.

18. The composition of claim 1 comprising a dosage of about 160 mg of fenofibrate, wherein following administration to fasting human subjects the blood levels of fenofibric acid are at least:
   (a) 1.0 µg/mL at one hour;
   (b) 6.5 µg/mL at two hours;
   (c) 7.0 µg/mL at three hours; and
   (d) 1.5 µg/mL at twenty-four hours.

19. The composition of claim 1 comprising a dosage of about 160 mg of fenofibrate, wherein following administration to high fat fed human subjects the blood levels of fenofibric acid are at least 4.5 µg/mL at one hour.

20. The composition of claim 1 comprising a dosage of about 160 mg of fenofibrate, wherein following administration to high fat fed human subjects the blood levels of fenofibric acid are at least 3.0 µg/mL at two hours.

21. The composition of claim 1 comprising a dosage of about 160 mg of fenofibrate, wherein following administration to high fat fed human subjects the blood levels of fenofibric acid are at least 6.0 µg/mL at four hours.

22. The composition of claim 1 comprising a dosage of about 160 mg of fenofibrate, wherein following administration to high fat fed human subjects the blood levels of fenofibric acid are at least 6.5 µg/mL at five hours.

23. The composition of claim 1 comprising a dosage of about 160 mg of fenofibrate, wherein following administration to high fat fed human subjects the blood levels of fenofibric acid are at least 1.5 µg/mL at twenty-four hours.

24. The composition of claim 1 comprising a dosage of about 160 mg of fenofibrate, wherein following administration to high fat fed human subjects the blood levels of fenofibric acid are at least:
(a) 4.5 μg/mL at one hour;
(b) 3.0 μg/mL at two hours;
(c) 6.0 μg/mL at four hours;
(d) 6.5 μg/mL at five hours; and
(e) 1.5 μg/mL at twenty-four hours.

25. The composition of claim 1, wherein the fenofibrate is selected from the group consisting of a crystalline phase, an amorphous phase, a semi-crystalline phase, a semi-amorphous phase, and mixtures thereof.

26. The composition of claim 1, wherein the D50 particle size of the particles of fenofibrate is selected from the group consisting of less than about 400 nm, less than about 300 nm, less than about 250 nm, less than about 200 nm, less than about 150 nm, less than about 100 nm, less than about 75 nm, and less than about 50 nm.

27. The composition of claim 1, wherein the particles of fenofibrate have a particle size in which the $D_{99}$ is less than about 500 nm.

28. The composition of claim 1, wherein the particles of fenofibrate have a particle size in which the $D_{50}$ is less than about 350 nm.

29. The composition of claim 1, wherein the particles of fenofibrate have a mean particle size of less than about 100 nm.

30. The composition of claim 1, wherein the composition is formulated for administration selected from the group consisting of oral, pulmonary, rectal, opthalmic, colonic, parenteral, intracisternal, intravaginal, intraperitoneal, local, buccal, nasal, and topical administration.

31. The composition of claim 1 formulated into a dosage form selected from the group consisting of liquid dispersions, oral suspensions, gels, aerosols, ointments, creams, tablets, and capsules.

32. The composition of claim 31 formulated into a dosage form selected from the group consisting of tablets and capsules.

33. The composition of claim 32 formulated into a tablet.

34. The composition of claim 1 formulated into a dosage form selected from the group consisting of controlled release formulations, fast melt formulations, lyophilized formulations, delayed release formulations, extended release formulations, pulsatile release formulations, and mixed immediate release and controlled release formulations.

35. The composition of claim 1 further comprising one or more pharmaceutically acceptable excipients, carriers, or a combination thereof.

36. The composition of claim 1, wherein within about 5 minutes at least about 20% of the composition is dissolved, wherein dissolution is measured in a discriminating aqueous media comprising sodium lauryl sulfate at 0.025 M, and wherein the rotating blade method (European Pharmacopoeia) is used to measure dissolution.

37. The composition of claim 1, wherein within about 10 minutes at least about 40% of the composition is dissolved, wherein dissolution is measured in a discriminating aqueous media comprising sodium lauryl sulfate at 0.025 M, and wherein the rotating blade method (European Pharmacopoeia) is used to measure dissolution.

38. The composition of claim 1, wherein within about 20 minutes at least about 70% of the composition is dissolved, wherein dissolution is measured in a discriminating aqueous media comprising sodium lauryl sulfate at 0.025 M, and wherein the rotating blade method (European Pharmacopoeia) is used to measure dissolution.

39. The composition of claim 1, wherein:
(a) within about 5 minutes at least about 30% of the composition is dissolved;
(b) within about 10 minutes at least about 70% of the composition is dissolved; and
(c) within about 20 minutes at least about 90% of the composition is dissolved,
wherein dissolution is measured in a discriminating aqueous media comprising sodium lauryl sulfate at 0.025 M, and wherein the rotating blade method (European Pharmacopoeia) is used to measure dissolution.

40. The composition of claim 1, wherein:
(a) within about 5 minutes at least about 40% of the composition is dissolved;
(b) within about 10 minutes at least about 80% of the composition is dissolved; and
(c) within about 20 minutes at least about 100% of the composition is dissolved,
wherein dissolution is measured in a discriminating aqueous media comprising sodium lauryl sulfate at 0.025 M, and wherein the rotating blade method (European Pharmacopoeia) is used to measure dissolution.

41. The composition of claim 1, additionally comprising one or more active agents selected from the group consisting of HMG CoA reductase inhibitors and antihypertensives.

42. The composition of claim 1, wherein within about 5 minutes at least about 30% of the composition is dissolved, wherein dissolution is measured in a discriminating aqueous media comprising sodium lauryl sulfate at 0.025 M, and wherein the rotating blade method (European Pharmacopoeia) is used to measure dissolution.

43. The composition of claim 1, wherein within about 5 minutes at least about 40% of the composition is dissolved, wherein dissolution is measured in a discriminating aqueous media comprising sodium lauryl sulfate at 0.025 M, and wherein the rotating blade method (European Pharmacopoeia) is used to measure dissolution.

44. The composition of claim 1, wherein within about 10 minutes at least about 50% of the composition is dissolved, wherein dissolution is measured in a discriminating aqueous media comprising sodium lauryl sulfate at 0.025 M, and wherein the rotating blade method (European Pharmacopoeia) is used to measure dissolution.

45. The composition of claim 1, wherein within about 10 minutes at least about 60% of the composition is dissolved, wherein dissolution is measured in a discriminating aqueous media comprising sodium lauryl sulfate at 0.025 M, and wherein the rotating blade method (European Pharmacopoeia) is used to measure dissolution.

46. The composition of claim 1, wherein within about 10 minutes at least about 70% of the composition is dissolved, wherein dissolution is measured in a discriminating aqueous media comprising sodium lauryl sulfate at 0.025 M, and wherein the rotating blade method (European Pharmacopoeia) is used to measure dissolution.

47. The composition of claim 1, wherein within about 10 minutes at least about 80% of the composition is dissolved, wherein dissolution is measured in a discriminating aqueous media comprising sodium lauryl sulfate at 0.025 M, and wherein the rotating blade method (European Pharmacopoeia) is used to measure dissolution.

48. The composition of claim 1, wherein within about 20 minutes at least about 80% of the composition is dissolved, wherein dissolution is measured in a discriminating aqueous media comprising sodium lauryl sulfate at 0.025 M, and wherein the rotating blade method (European Pharmacopoeia) is used to measure dissolution.

49. The composition of claim 1, wherein within about 20 minutes at least about 90% of the composition is dissolved, wherein dissolution is measured in a discriminating aqueous media comprising sodium lauryl sulfate at 0.025 M, and wherein the rotating blade method (European Pharmacopoeia) is used to measure dissolution.

50. The composition of claim 1, wherein within about 20 minutes at least about 100% of the composition is dissolved, wherein dissolution is measured in a discriminating aqueous media comprising sodium lauryl sulfate at 0.025 M, and wherein the rotating blade method (European Pharmacopoeia) is used to measure dissolution.

51. The composition of claim 1, wherein upon administration the composition redisperses such that the redispersed particles of fenofibrate or a salt thereof have a D50 particle size selected from the group consisting of less than about 500 nm, less than about 400 nm, less than about 300 nm, less than about 250 nm, less than about 200 nm, less than about 150 nm, less than about 100 nm, less than about 75 nm, and less than about 50 nm.

52. The composition of claim 1, wherein the composition redisperses in a biorelevant media such that the redispersed particles of fenofibrate or a salt thereof have a D50 particle size selected from the group consisting of less than about 500 nm, less than about 400 nm, less than about 300 nm, less than about 250 nm, less than about 200 nm, less than about 150 nm, less than about 100 nm, less than about 75 nm, and less than about 50 nm.

53. A stable fenofibrate composition for oral administration comprising:
(a) particles of fenofibrate having a D50 particle size of less than about 500 nm in a dosage form for oral administration which is a tablet or capsule of about 145 mg of fenofibrate, and
(b) at least one surface stabilizer,
wherein:
(i) the composition exhibits bioequivalence upon administration to a human subject in a fed state as compared to administration to a human subject in a fasted state; where bioequivalency is established by:
(a) a 90% Confidence Interval for AUC which is between 80% and 125%, and
(b) a 90% Confidence Interval for $C_{max}$, which is between 80% and 125%;
(ii) the composition redisperses in a biorelevant media; and
(iii) the composition is phospholipid-free.

54. The composition of claim 1, comprising at least one primary surface stabilizer and at least one secondary surface stabilizer.

55. The composition of claim 1, wherein the surface stabilizer is selected from the group consisting of an anionic surface stabilizer, a non-ionic surface stabilizer, a cationic surface stabilizer, a zwitterionic surface stabilizer, and an ionic surface stabilizer.

56. The composition of claim 1, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, non-crystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-cholesterol, PEG-cholesterol derivative, PEG-vitamin A, and random copolymers of vinyl acetate and vinyl pyrrolidone.

57. The composition of claim 1, wherein the at least one cationic surface stabilizer is selected from the group consisting of a polymer, a biopolymer, a polysaccharide, a cellulosic, an alginate, a nonpolymeric compound, cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium-10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, polyquaternium compounds, alkyl pyridiium salts; amines, amine salts, amine oxides, imide azolinium salts, protonated quaternary acrylamides, methylated quaternary polymers, and cationic guar.

58. The composition of claim 1, comprising hypromellose, dioctyl sodium sulfosuccinate, and sodium lauryl sulfate as surface stabilizers.

59. The composition of claim 53, comprising at least one primary surface stabilizer and at least one secondary surface stabilizer.

60. The composition of claim 53, wherein the surface stabilizer is selected from the group consisting of an anionic surface stabilizer, a non-ionic surface stabilizer, a cationic surface stabilizer, a zwitterionic surface stabilizer, and an ionic surface stabilizer.

61. The composition of claim 53, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, noncrystalline cellulose, magnesium aluminum silicate, triethanolamine, polyvinyl alcohol, polyvinylpyrrolidone, 4-(1,1, 3,3-tetramethylbutyl)-phenol polymer with ethylene oxide and formaldehyde, poloxamers; poloxamines, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-cholesterol, PEG-cholesterol derivative, PEG-vitamin A, and random copolymers of vinyl acetate and vinyl pyrrolidone.

62. The composition of claim 53, wherein the at least one cationic surface stabilizer is selected from the group consisting of a polymer, a biopolymer, a polysaccharide, a cellulosic, an alginate, a nonpolymeric compound, cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quartemary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium-10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, polyquaternium compounds, alkyl pyridinium salts; amines, amine salts, amine oxides, imide azolinium salts, protonated quaternary acrylamides, methylated quaternary polymers, and cationic guar.

63. The composition of claim 53, comprising hypromellose, dioctyl sodium sulfosuccinate, and sodium lauryl sulfate as surface stabilizers.

64. A stable fenofibrate composition for oral administration comprising:
(a) particles of fenofibrate having a mean particle size of less than about 500 nm, and
(b) at least one surface stabilizer, wherein, the surface stabilizer is not selected from the group consisting of sorbitan esters, polyoxyethylene castor oil derivatives, polyoxyethylene sorbitan fatty acid esters and polyoxylene stearates,
wherein:
(i) the composition exhibits bioequivalence upon administration to a human subject in a fed state as compared to administration to a human subject in a fasted state; where bioequivalency is established by:
(a) a 90% Confidence Interval for AUC which is between 80% and 125%, and
(b) a 90% Confidence Interval for $C_{max}$, which is between 80% and 125%;
(ii) the composition redisperses in a biorelevant media; and
(iii) the composition is phospholipid-free.

65. The composition of claim 64, which is bioequivalent to a micronized 54 mg fenofibrate oral solid dosage form.

66. The composition of claim 64, which is bioequivalent to a micronized 160 mg fenofibrate oral solid dosage form.

67. The composition of claim 66, which is a single daily dose.

68. The composition of claim 64, which is bioequivalent to a micronized 200 mg fenofibrate oral solid dosage form.

69. The composition of claim 68, which is a single daily dose.

70. The composition of claim 64, wherein the difference in AUC of the fenofibrate composition, when administered to a human subject in the fed versus the fasted state, is selected from the group consisting of less than about 35%, less than about 30%, less than about 25%, less than about 20%, less than about 15%, less than about 10%, less than about 5%, and less than about 3%.

71. The composition of claim 64, which when administered to a human subject at a dose of about 160 mg presents an AUC of about 139 μg/mL.h.

72. The composition of claim 64 which exhibits a $T_{max}$ after administration to fasting human subjects selected from the group consisting of less than about 6 hours, less than about 5 hours, less than about 4 hours, less than about 3 hours, less than about 2 hours, less than about 1 hour, and less than about 30 minutes.

73. The composition of claim 64, wherein in comparative pharmacokinetic testing with a 160 mg micronized fenofibrate tablet or 200 mg micronized fenofibate capsule, which are standard commercial formulations of microcrystalline fenofibrate, the composition of claim 136 exhibits a $T_{max}$ selected from the group consisting of less than about 90%, less than about 80%, less than about 70%, less than about 50%, less than about 30%, and less than about 25% of the $T_{max}$ exhibited by the micronized fenofibate tablet or capsule.

74. The composition of claim 64, wherein the fenofibrate is present in an amount selected from the group consisting of:
(a) about 50 to about 500 g of fenofibrate per kg of composition;
(b) about 100 to about 300 g of fenofibrate per kg of composition;
(c) about 200 to about 225 g of fenofibrate per kg of composition; and
(d) about 119 to about 224 g of fenofibrate per kg of composition.

75. The composition of claim 64 comprising a dosage of about 145 mg of fenofibrate, wherein:
(a) the dosage is therapeutically effective; and
(b) the composition is bioequivalent to a 160 mg micronized fenofibate tablet or 200 mg micronized fenofibate capsule, wherein bioequivalency, when administered to a human, is established by a 90% Confidence Interval of between 0.80 and 1.25 for both $C_{max}$ and AUC.

76. The composition of claim 64 comprising a dosage of about 48 mg of fenofibrate, wherein:
(a) the dosage is therapeutically effective; and
(b) the composition is bioequivalent to a 54 mg micronized fenofibate tablet, wherein bioequivalency, when administered to a human, is established by a 90% Confidence Interval of between 0.80 and 1.25 for both $C_{max}$ and AUC.

77. The composition of claim 64 comprising a dosage of about 160 mg of fenofibrate, wherein following administration to fasting human subjects the blood levels of fenofibric acid are at least 4.5 μg/mL at one hour.

78. The composition of claim 64 comprising a dosage of about 160 mg of fenofibrate, wherein following administration to fasting human subjects the blood levels of. fenofibric acid are at least 6.5 μg/mL at two hours.

79. The composition of claim 64 comprising a dosage of about 160 mg of fenofibrate, wherein following administration to fasting human subjects the blood levels of fenofibric acid are at least 7.0 μg/mL at three hours.

80. The composition of claim 64 comprising a dosage of about 160 mg of fenofibrate, wherein following administration to fasting human subjects the blood levels of fenofibric acid are at least 1.5 μg/mL at twenty-four hours.

81. The composition of claim 64 comprising a dosage of about 160 mg of fenofibrate, wherein following administration to fasting human subjects the blood levels of fenofibric acid are at least:
(a) 1.0 μg/mL at one hour;
(b) 6.5 μg/mL at two hours;
(c) 7.0 μg/mL at three hours; and
(d) 1.5 μg/mL at twenty-four hours.

82. The composition of claim 64 comprising a dosage of about 160 mg of fenofibrate, wherein following administration to high fat fed human subjects the blood levels of fenofibric acid are at least 4.5 μg/mL at one hour.

83. The composition of claim 64 comprising a dosage of about 160 mg of fenofibrate, wherein following administration to high fat fed human subjects the blood levels of fenofibric acid are at least 3.0 g/mL at two hours.

84. The composition of claim 64 comprising a dosage of about 160 mg of fenofibrate, wherein following administration to high fat fed human subjects the blood levels of fenofibric acid are at least 6.0 μg/mL at four hours.

85. The composition of claim 64 comprising a dosage of about 160 mg of fenofibrate, wherein following administration to high fat fed human subjects the blood levels of fenofibric acid are at least 6.5 μg/mL at five hours.

86. The composition of claim 64 comprising a dosage of about 160 mg of fenofibrate, wherein following administration to high fat fed human subjects the blood levels of fenofibric acid are at least 1.5 μg/mL at twenty-four hours.

87. The composition of claim 64 comprising a dosage of about 160 mg of fenofibrate, wherein following administration to high fat fed human subjects the blood levels of fenofibric acid are at least:
(a) 4.5 μg/mL at one hour;
(b) 3.0 μg/mL at two hours;
(c) 6.0 μg/mL at four hours;
(d) 6.5 μg/mL at five hours; and
(e) 1.5 μg/mL at twenty-four hours.

88. The composition of claim 64, wherein the fenofibrate is selected from the group consisting of a crystalline phase, an amorphous phase, a semi-crystalline phase, a semi-amorphous phase, and mixtures thereof.

89. The composition of claim 64, wherein the mean particle size of the particles of fenofibrate is selected from the group consisting of less than about 400 nm, less than about 300 nm, less than about 250 nm, less than about 200 nm, less than about 150 nm, less than about 100 nm, less than about 75 nm, and less than about 50 nm.

90. The composition of claim 64, wherein the particles of fenofibrate have a particle size in which the $D_{99}$ is less than about 500 nm.

91. The composition of claim 64, wherein the particles of fenofibrate have a particle size in which the $D_{50}$ is less than about 350 nm.

92. The composition of claim 64, wherein the particles of fenofibrate have a mean particle size of less than about 100 nm.

93. The composition of claim 64, wherein the composition is formulated for administration selected from the group consisting of oral, pulmonary, rectal, opthalmic, colonic, parenteral, intracistemal, intravaginal, intraperitoneal, local, buccal, nasal, and topical administration.

94. The composition of claim 64 formulated into a dosage form selected from the group consisting of liquid dispersions, oral suspensions, gels, aerosols, ointments, creams, tablets, and capsules.

95. The composition of claim 94 formulated into a dosage form selected from the group consisting of tablets and capsules.

96. The composition of claim 95 formulated into a tablet.

97. The composition of claim 64 formulated into a dosage form selected from the group consisting of controlled release formulations, fast melt formulations, lyophilized formulations, delayed release formulations, extended release formulations, pulsatile release formulations, and mixed immediate release and controlled release formulations.

98. The composition of claim 64 further comprising one or more pharmaceutically acceptable excipients, carriers, or a combination thereof.

99. The composition of claim 64, wherein within about 5 minutes at least about 20% of the composition is dissolved, wherein dissolution is measured in a discriminating aqueous media comprising sodium lauryl sulfate at 0.02 5 M, and wherein the rotating blade method (European Pharmacopoeia) is used to measure dissolution.

100. The composition of claim 64, wherein within about 10 minutes at least about 40% of the composition is dissolved, wherein dissolution is measured in a discriminating aqueous media comprising sodium lauryl sulfate at 0.025 M, and wherein the rotating blade method (European Pharmacopoeia) is used to measure dissolution.

101. The composition of claim 64, wherein within about 20 minutes at least about 70% of the composition is dissolved, wherein dissolution is measured in a discriminating aqueous media comprising sodium lauryl sulfate at 0.025 M, and wherein the rotating blade method (European Pharmacopoeia) is used to measure dissolution.

102. The composition of claim 64, wherein:
 (a) within about 5 minutes at least about 30% of the composition is dissolved;
 (b) within about 10 minutes at least about 70% of the composition is dissolved; and
 (c) within about 20 minutes at least about 90% of the composition is dissolved,
 wherein dissolution is measured in a discriminating aqueous media comprising sodium lauryl sulfate at 0.025 M, and wherein the rotating blade method (European Pharmacopoeia) is used to measure dissolution.

103. The composition of claim 64, wherein:
 (a) within about 5 minutes at least about 40% of the composition is dissolved;
 (b) within about 10 minutes at least about 80% of the composition is dissolved; and
 (c) within about 20 minutes at least about 100% of the composition is dissolved,
 wherein dissolution is measured in a discriminating aqueous media comprising sodium lauryl sulfate at 0.025 M, and wherein the rotating blade method (European Pharmacopoeia) is used to measure dissolution.

104. The composition of claim 64, additionally comprising one or more active agents selected from the group consisting of HMG CoA reductase inhibitors and antihypertensives.

105. The composition of claim 64, wherein within about 5 minutes at least about 30% of the composition is dissolved, wherein dissolution is measured in a discriminating aqueous media comprising sodium lauryl sulfate at 0.025 M, and wherein the rotating blade method (European Pharmacopoeia) is used to measure dissolution.

106. The composition of claim 64, wherein within about 5 minutes at least about 40% of the composition is dissolved, wherein dissolution is measured in a discriminating aqueous media comprising sodium lauryl sulfate at 0.025 M, and wherein the rotating blade method (European Pharmacopoeia) is used to measure dissolution.

107. The composition of claim 64, wherein within about 10 minutes at least about 50% of the composition is dissolved, wherein dissolution is measured in a discriminating aqueous media comprising sodium lauryl sulfate at 0.025 M, and wherein the rotating blade method (European Pharmacopoeia) is used to measure dissolution.

108. The composition of claim 64, wherein within about 10 minutes at least about 60% of the composition is dissolved, wherein dissolution is measured in a discriminating aqueous media comprising sodium lauryl sulfate at 0.025 M, and wherein the rotating blade method (European Pharmacopoeia) is used to measure dissolution.

109. The composition of claim 64, wherein within about 10 minutes at least about 70% of the composition is dissolved, wherein dissolution is measured in a discriminating aqueous media comprising sodium lauryl sulfate at 0.025 M, and wherein the rotating blade method (European Pharmacopoeia) is used to measure dissolution.

110. The composition of claim 64, wherein within about 10 minutes at least about 80% of the composition is dissolved, wherein dissolution is measured in a discriminating aqueous media comprising sodium lauryl sulfate at 0.025 M, and wherein the rotating blade method (European Pharmacopoeia) is used to measure dissolution.

111. The composition of claim 64, wherein within about 20 minutes at least about 80% of the composition is dissolved, wherein dissolution is measured in a discriminating aqueous media comprising sodium lauryl sulfate at 0.025 M, and wherein the rotating blade method (European Pharmacopoeia) is used to measure dissolution.

112. The composition of claim 64, wherein within about 20 minutes at least about 90% of the composition is dissolved, wherein dissolution is measured in a discriminating aqueous media comprising sodium lauryl sulfate at 0.025 M, and wherein the rotating blade method (European Pharmacopoeia) is used to measure dissolution.

113. The composition of claim 64, wherein within about 20 minutes at least about 100% of the composition is dissolved, wherein dissolution is measured in a discriminating aqueous media comprising sodium lauryl sulfate at 0.025 M, and wherein the rotating blade method (European Pharmacopoeia) is used to measure dissolution.

114. The composition of claim 64, wherein upon administration the composition redisperses such that the redispersed particles of fenofibrate or a salt thereof have a mean particle size selected from the group consisting of less than about 500 nm, less than about 400 nm, less than about 300 nm, less than about 250 nm, less than about 200 nm, less than about 150 nm, less than about 100 nm, less than about 75 nm, and less than about 50 nm.

115. The composition of claim 64, wherein the composition redisperses in a biorelevant media such that the redispersed particles of fenofibrate or a salt thereof have a mean particle size selected from the group consisting of less than about 500 nm, less than about 400 nm, less than about 300 nm, less than about 250 nm, less than about 200 nm, less than about 150 nm, less than about 100 nm, less than about 75 nm, and less than about 50 nm.

116. The composition of claim 64, comprising at least one primary surface stabilizer and at least one secondary surface stabilizer.

117. The composition of claim 64, wherein the surface stabilizer is selected from the group consisting of an anionic surface stabilizer, a non-ionic surface stabilizer, a cationic surface stabilizer, a zwitterionic surface stabilizer, and an ionic surface stabilizer.

118. The composition of claim 64, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, polyoxyethylene alkyl ethers, polyethylene glycols, dodecyl trimethyl ammonium bromide, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, non-crystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-cholesterol, PEG-cholesterol derivative, PEG-vitamin A, and random copolymers of vinyl acetate and vinyl pyrrolidone.

119. The composition of claim 64, wherein the at least one cationic surface stabilizer is selected from the group consisting of a polymer, a biopolymer, a polysaccharide, a cellulosic, an alginate, a nonpolymeric compound, cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quartemary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium-10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, polyquaternium compounds, alkyl pyridinium salts; amines, amine salts, amine oxides, imide azolinium salts, protonated quaternary acrylamides, methylated quaternary polymers, and cationic guar.

120. The composition of claim 64, comprising hypromellose, dioctyl sodium sulfosuccinate, and sodium lauryl sulfate as surface stabilizers.

121. A stable fenofibrate composition for oral administration comprising:
(a) particles of fenofibrate having a D90 particle size of less than about 700 nm, and
(b) at least one surface stabilizer,
wherein:
(i) the composition exhibits bioequivalence upon administration to a human subject in a fed state as compared to administration to a human subject in a fasted state; where bioequivalency is established by:
(a) a 90% Confidence Interval for AUC which is between 80% and 125%, and
(b) a 90% Confidence Interval for $C_{max}$, which is between 80% and 125%;
(ii) the composition redisperses in a biorelevant media; and
(iii) the composition is phospholipid-free.

122. The composition of claim 121, which is bioequivalent to a micronized 54 mg fenofibrate oral solid dosage form.

123. The composition of claim 121, which is bioequivalent to a micronized 160 mg fenofibrate oral solid dosage form.

124. The composition of claim 123, which is a single daily dose.

125. The composition of claim 121, which is bioequivalent to a micronized 200 mg fenofibrate oral solid dosage form.

126. The composition of claim 125, which is a single daily dose.

127. The composition of claim 121, wherein the difference in AUC of the fenofibrate composition, when administered to a human subject in the fed versus the fasted state, is selected from the group consisting of less than about 35%, less than about 30%, less than about 25%, less than about 20%, less than about 15%, less than about 10%, less than about 5%, and less than about 3%.

128. The composition of claim 121, which when administered to a human subject at a dose of about 160 mg presents an AUC of about 139 µg/mL.h.

129. The composition of claim 121 which exhibits a $T_{max}$ after administration to fasting human subjects selected from the group consisting of less than about 6 hours, less than about 5 hours, less than about 4 hours, less than about 3 hours, less than about 2 hours, less than about 1 hour, and less than about 30 minutes.

130. The composition of claim 121, wherein in comparative pharmacokinetic testing with a 160 mg micronized fenofibrate tablet or 200 mg micronized fenofibrate capsule, which are standard commercial formulations of microcrystalline fenofibrate, the composition of claim 136 exhibits a $T_{max}$ selected from the group consisting of less than about 90%, less than about 80%, less than about 70%, less than about 50%, less than about 30%, and less than about 25% of the $T_{max}$ exhibited by the micronized fenofibrate tablet or capsule.

131. The composition of claim 121, wherein the fenofibrate is present in an amount selected from the group consisting of:
 (a) about 50 to about 500 g of fenofibrate per kg of composition;
 (b) about 100 to about 300 g of fenofibrate per kg of composition;
 (c) about 200 to about 225 g of fenofibrate per kg of composition; and
 (d) about 119 to about 224 g of fenofibrate per kg of composition.

132. The composition of claim 121 comprising a dosage of about 145 mg of fenofibrate, wherein:
 (a) the dosage is therapeutically effective; and
 (b) the composition is bioequivalent to a 160 mg micronized fenofibate tablet or 200 mg micronized fenofibate capsule, wherein bioequivalency, when administered to a human, is established by a 90% Confidence Interval of between 0.80 and 1.25 for both $C_{max}$ and AUC.

133. The composition of claim 121 comprising a dosage of about 48 mg of fenofibrate, wherein:
 (a) the dosage is therapeutically effective; and
 (b) the composition is bioequivalent to a 54 mg micronized fenofibate tablet, wherein bioequivalency, when administered to a human, is established by a 90% Confidence Interval of between 0.80 and 1.25 for both $C_{max}$ and AUC.

134. The composition of claim 121 comprising a dosage of about 160 mg of fenofibrate, wherein following administration to fasting human subjects the blood levels of fenofibric acid are at least 4.5 µg/mL at one hour.

135. The composition of claim 121 comprising a dosage of about 160 mg of fenofibrate, wherein following administration to fasting human subjects the blood levels of fenofibric acid are at least 6.5 µg/mL at two hours.

136. The composition of claim 121 comprising a dosage of about 160 mg of fenofibrate, wherein following administration to fasting human subjects the blood levels of fenofibric acid are at least 7.0 µg/mL at three hours.

137. The composition of claim 121 comprising a dosage of about 160 mg of fenofibrate, wherein following administration to fasting human subjects the blood levels of fenofibric acid are at least 1.5 µg/mL at twenty-four hours.

138. The composition of claim 121 comprising a dosage of about 160 mg of fenofibrate, wherein following administration to fasting human subjects the blood levels of fenofibric acid are at least:
 (a) 1.0 µg/mL at one hour;
 (b) 6.5 µg/mL at two hours;
 (c) 7.0 µg/mL at three hours; and
 (d) 1.5 µg/mL at twenty-four hours.

139. The composition of claim 121 comprising a dosage of about 160 mg of fenofibrate, wherein following administration to high fat fed human subjects the blood levels of fenofibric acid are at least 4.5 µg/mL at one hour.

140. The composition of claim 121 comprising a dosage of about 160 mg of fenofibrate, wherein following administration to high fat fed human subjects the blood levels of fenofibric acid are at least 3.0 µg/mL at two hours.

141. The composition of claim 121 comprising a dosage of about 160 mg of fenofibrate, wherein following administration to high fat fed human subjects the blood levels of fenofibric acid are at least 6.0 µg/mL at four hours.

142. The composition of claim 121 comprising a dosage of about 160 mg of fenofibrate, wherein following administration to high fat fed human subjects the blood levels of fenofibric acid are at least 6.5 µg/mL at five hours.

143. The composition of claim 121 comprising a dosage of about 160 mg of fenofibrate, wherein following administration to high fat fed human subjects the blood levels of fenofibric acid are at least 1.5 µg/mL at twenty-four hours.

144. The composition of claim 121 comprising a dosage of about 160 mg of fenofibrate, wherein following administration to high fat fed human subjects the blood levels of fenofibric acid are at least:
 (a) 4.5 µg/mL at one hour;
 (b) 3.0 µg/mL at two hours;
 (c) 6.0 µg/mL at four hours;
 (d) 6.5 µg/mL at five hours; and
 (e) 1.5 µg/mL at twenty-four hours.

145. The composition of claim 121, wherein the fenofibrate is selected from the group consisting of a crystalline phase, an amorphous phase, a semi-crystalline phase, a semi-amorphous phase, and mixtures thereof.

146. The composition of claim 121, wherein the D90 particle size of the particles of fenofibrate is selected from the group consisting of less than about 400 nm, less than about 300 nm, less than about 250 nm, less than about 200 nm, less than about 150 nm, less than about 100 nm, less than about 75 nm, and less than about 50 nm.

147. The composition of claim 121, wherein the particles of fenofibrate have a particle size in which the $D_{99}$ is less than about 500 nm.

148. The composition of claim 121, wherein the particles of fenofibrate have a particle size in which the $D_{50}$ is less than about 350 nm.

149. The composition of claim 121, wherein the particles of fenofibrate have a mean particle size of less than about 100 nm.

150. The composition of claim 121, wherein the composition is formulated for administration selected from the group consisting of oral, pulmonary, rectal, opthalmic, colonic, parenteral, intracistemal, intravaginal, intraperitoneal, local, buccal, nasal, and topical administration.

151. The composition of claim 121 formulated into a dosage form selected from the group consisting of liquid dispersions, oral suspensions, gels, aerosols, ointments, creams, tablets, and capsules.

152. The composition of claim 151 formulated into a dosage form selected from the group consisting of tablets and capsules.

153. The composition of claim 152 formulated into a tablet.

154. The composition of claim 121 formulated into a dosage form selected from the group consisting of controlled release formulations, fast melt formulations, lyophilized formulations, delayed release formulations, extended release formulations, pulsatile release formulations, and mixed immediate release and controlled release formulations.

155. The composition of claim 121 further comprising one or more pharmaceutically acceptable excipients, carriers, or a combination thereof.

156. The composition of claim 121, wherein within about 5 minutes at least about 20% of the composition is dissolved, wherein dissolution is measured in a discriminating aqueous media comprising sodium lauryl sulfate at 0.025 M, and wherein the rotating blade method (European Pharmacopoeia) is used to measure dissolution.

157. The composition of claim 121, wherein within about 10 minutes at least about 40% of the composition is dissolved, wherein dissolution is measured in a discriminating aqueous media comprising sodium lauryl sulfate at 0.025 M, and wherein the rotating blade method (European Pharmacopoeia) is used to measure dissolution.

158. The composition of claim 121, wherein within about 20 minutes at least about 70% of the composition is dissolved, wherein dissolution is measured in a discriminating aqueous media comprising sodium lauryl sulfate at 0.025 M, and wherein the rotating blade method (European Pharmacopoeia) is used to measure dissolution.

159. The composition of claim 121, wherein:
(a) within about 5 minutes at least about 30% of the composition is dissolved;
(b) within about 10 minutes at least about 70% of the composition is dissolved; and
(c) within about 20 minutes at least about 90% of the composition is dissolved,
wherein dissolution is measured in a discriminating aqueous media comprising sodium lauryl sulfate at 0.025 M, and wherein the rotating blade method (European Pharmacopoeia) is used to measure dissolution.

160. The composition of claim 121, wherein:
(a) within about 5 minutes at least about 40% of the composition is dissolved;
(b) within about 10 minutes at least about 80% of the composition is dissolved; and
(c) within about 20 minutes at least about 100% of the composition is dissolved,
wherein dissolution is measured in a discriminating aqueous media comprising sodium lauryl sulfate at 0.025 M, and wherein the rotating blade method (European Pharmacopoeia) is used to measure dissolution.

161. The composition of claim 121, additionally comprising one or more active agents selected from the group consisting of HMG CoA reductase inhibitors and antihypertensives.

162. The composition of claim 121, wherein within about 5 minutes at least about 30% of the composition is dissolved, wherein dissolution is measured in a discriminating aqueous media comprising sodium lauryl sulfate at 0.025 M, and wherein the rotating blade method (European Pharmacopoeia) is used to measure dissolution.

163. The composition of claim 121, wherein within about 5 minutes at least about 40% of the composition is dissolved, wherein dissolution is measured in a discriminating aqueous media comprising sodium lauryl sulfate at 0.025 M, and wherein the rotating blade method (European Pharmacopoeia) is used to measure dissolution.

164. The composition of claim 121, wherein within about 10 minutes at least about 50% of the composition is dissolved, wherein dissolution is measured in a discriminating aqueous media comprising sodium lauryl sulfate at 0.025 M, and wherein the rotating blade method (European Pharmacopoeia) is used to measure dissolution.

165. The composition of claim 121, wherein within about 10 minutes at least about 60% of the composition is dissolved, wherein dissolution is measured in a discriminating aqueous media comprising sodium lauryl sulfate at 0.025 M, and wherein the rotating blade method (European Pharmacopoeia) is used to measure dissolution.

166. The composition of claim 121, wherein within about 10 minutes at least about 70% of the composition is dissolved, wherein dissolution is measured in a discriminating aqueous media comprising sodium lauryl sulfate at 0.025 M, and wherein the rotating blade method (European Pharmacopoeia) is used to measure dissolution.

167. The composition of claim 121, wherein within about 10 minutes at least about 80% of the composition is dissolved, wherein dissolution is measured in a discriminating aqueous media comprising sodium lauryl sulfate at 0.025 M, and wherein the rotating blade method (European Pharmacopoeia) is used to measure dissolution.

168. The composition of claim 121, wherein within about 20 minutes at least about 80% of the composition is dissolved, wherein dissolution is measured in a discriminating aqueous media comprising sodium lauryl sulfate at 0.025 M, and wherein the rotating blade method (European Pharmacopoeia) is used to measure dissolution.

169. The composition of claim 121, wherein within about 20 minutes at least about 90% of the composition is dissolved, wherein dissolution is measured in a discriminating aqueous media comprising sodium lauryl sulfate at 0.025 M, and wherein the rotating blade method (European Pharmacopoeia) is used to measure dissolution.

170. The composition of claim 121, wherein within about 20 minutes at least about 100% of the composition is dissolved, wherein dissolution is measured in a discriminating aqueous media comprising sodium lauryl sulfate at 0.025 M, and wherein the rotating blade method (European Pharmacopoeia) is used to measure dissolution.

171. The composition of claim 121, wherein upon administration the composition redisperses such that the redispersed particles of fenofibrate or a salt thereof have a D90 particle size selected from the group consisting of less than about 500 nm, less than about 400 nm, less than about 300 nm, less than about 250 nm, less than about 200 nm, less than about 150 nm, less than about 100 nm, less than about 75 nm, and less than about 50 nm.

172. The composition of claim 121, wherein the composition redisperses in a biorelevant media such that the redispersed particles of fenofibrate or a salt thereof have a D90 particle size selected from the group consisting of less than about 500 nm, less than about 400 nm, less than about 300 nm, less than about 250 nm, less than about 200 nm, less than about 150 nm, less than about 100 nm, less than about 75 nm, and less than about 50 nm.

173. The composition of claim 121, comprising at least one primary surface stabilizer and at least one secondary surface stabilizer.

174. The composition of claim 121, wherein the surface stabilizer is selected from the group consisting of an anionic surface stabilizer, a non-ionic surface stabilizer, a cationic surface stabilizer, a zwitterionic surface stabilizer, and an ionic surface stabilizer.

175. The composition of claim 121, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, non-crystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-cholesterol, PEG-cholesterol derivative, PEG-vitamin A, and random copolymers of vinyl acetate and vinyl pyrrolidone.

176. The composition of claim 121, wherein the at least one cationic surface stabilizer is selected from the group consisting of a polymer, a biopolymer, a polysaccharide, a cellulosic, an alginate, a nonpolymeric compound, cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quartemary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium-10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, polyquaternium compounds, alkyl pyridinium salts; amines, amine salts, amine oxides, imide azolinium salts, protonated quaternary acrylamides, methylated quaternary polymers, and cationic guar.

177. The composition of claim 121, comprising hypromellose, dioctyl sodium sulfosuccinate, and sodium lauryl sulfate as surface stabilizers.

178. A stable fenofibrate composition for oral administration comprising:
(a) particles of fenofibrate having a mean particle size of less than about 500 nm in a dosage form for oral administration which is a tablet or capsule of about 145 mg of fenofibrate, and
(b) at least one surface stabilizer,
wherein:
(i) the composition exhibits bioequivalence upon administration to a human subject in a fed state as compared to administration to a human subject in a fasted state; where bioequivalency is established by:
(a) a 90% Confidence Interval for AUC which is between 80% and 125%, and
(b) a 90% Confidence Interval for $C_{max}$, which is between 80% and 125%;
(ii) the composition redisperses in a biorelevant media; and
(iii) the composition is phospholipid-free.

179. The composition of claim 178, comprising at least one primary surface stabilizer and at least one secondary surface stabilizer.

180. The composition of claim 178, wherein the surface stabilizer is selected from the group consisting of an anionic surface stabilizer, a non-ionic surface stabilizer, a cationic surface stabilizer, a zwitterionic surface stabilizer, and an ionic surface stabilizer.

181. The composition of claim 178, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, non-crystalline cellulose, magnesium aluminum silicate, triethanolamine, polyvinyl alcohol, polyvinylpyrrolidone, 4-(1,1, 3,3-tetramethylbutyl)-phenol polymer with ethylene oxide and formaldehyde, poloxamers; poloxamines, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyrano side; octanoyl-N-methylglucamide; n-octyl-β-D-glucopyranoside; octyl β-D-thioglucopyranoside; lysozyme, PEG-cholesterol, PEG-cholesterol derivative, PEG-vitamin A, and random copolymers of vinyl acetate and vinyl pyrrolidone.

182. The composition of claim 178, wherein the at least one cationic surface stabilizer is selected from the group consisting of a polymer, a biopolymer, a polysaccharide, a cellulosic, an alginate, a nonpolymeric compound, cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quartemary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12}$-15dimethyl hydroxyethyl ammonium chloride, $C_{12}$-15dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12}$-18)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium-10, tetrabutylammonium bromide, benzyl trimethylammonium bromide, choline esters, benzalkonium chloride, stearalkonium chloride compounds, cetyl pyridinium bromide, cetyl pyridiium chloride, halide salts of quaternized polyoxyethylalkylamines, polyquaternium compounds, alkyl pyridinium salts; amines, amine salts, amine oxides, imide azolinium salts, protonated quaternary acrylamides, methylated quaternary polymers, and cationic guar.

183. The composition of claim 178, comprising hypromellose, dioctyl sodium sulfosuccinate, and sodium lauryl sulfate as surface stabilizers.

184. A stable fenofibrate composition for oral administration comprising:
(a) particles of fenofibrate having a D90 particle size of less than about 500 nm in a dosage form for oral administration which is a tablet or capsule of about 145 mg of fenofibrate, and
(b) at least one surface stabilizer,
wherein:
(i) the composition exhibits bioequivalence upon administration to a human subject in a fed state as compared to administration to a human subject in a fasted state; where bioequivalency is established by:
(a) a 90% Confidence Interval for AUC which is between 80% and 125%, and
(b) a 90% Confidence Interval for $C_{max}$, which is between 80% and 125%;
(ii) the composition redisperses in a biorelevant media; and
(iii) the composition is phospholipid-free.

185. The composition of claim 184, comprising at least one primary surface stabilizer and at least one secondary surface stabilizer.

186. The composition of claim 184, wherein the surface stabilizer is selected from the group consisting of an anionic surface stabilizer, a non-ionic surface stabilizer, a cationic surface stabilizer, a zwitterionic surface stabilizer, and an ionic surface stabilizer.

187. The composition of claim 184, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, non-crystalline cellulose, magnesium aluminum silicate, triethanolamine, polyvinyl alcohol, polyvinylpyrrolidone, 4-(1,1, 3,3-tetramethylbutyl)-phenol polymer with ethylene oxide and formaldehyde, poloxamers; poloxamines, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide;

n-noyl β-D-glucopyranoside; octanoyl-N-methylglucamide; n-octyl-β-D-glucopyranoside; octyl β-D-thioglucopyranoside; lysozyme, PEG-cholesterol, PEG-cholesterol derivative, PEG-vitamin A, and random copolymers of vinyl acetate and vinyl pyrrolidone.

188. The composition of claim 184, wherein the at least one cationic surface stabilizer is selected from the group consisting of a polymer, a biopolymer, a polysaccharide, a cellulosic, an alginate, a nonpolymeric compound, cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quartemary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12}$-15dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12}$-18)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12}$-14) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium-10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, polyquaternium compounds, alkyl pyridinium salts; amines, amine salts, amine oxides, imide azolinium salts, protonated quaternary acrylamides, methylated quaternary polymers, and cationic guar.

189. The composition of claim 184, comprising hypromellose, dioctyl sodium sulfosuccinate, and sodium lauryl sulfate as surface stabilizers.

* * * * *

UNITED STATES PATENT AND TRADEMARK OFFICE
CERTIFICATE OF CORRECTION

| | |
|---|---|
| PATENT NO. | : 7,276,249 B2 |
| APPLICATION NO. | : 10/444066 |
| DATED | : October 2, 2007 |
| INVENTOR(S) | : Tuula Ryde et al. |

It is certified that error appears in the above-identified patent and that said Letters Patent is hereby corrected as shown below:

IN THE DRAWINGS:

In both Figures 1 and 2, please change "200 M LFF" to -- 200 mg LFF --.

Column 9, line 23, change "ice" to -- i.e., --.

Column 16, lines 53-54, change "benzyl-di(2-chloroethyl)etbylammonium bromide" to -- benzyl-di(2-choloroethyl)ethylammonium bromide --.

Column 16, line 31, please delete "n-noyl b-D-glucopyranoside" and insert therefor -- n-nonyl b-D-glucopyranoside --.

Column 17, line 33, change "acrylarnides" to -- acrylamides --.

Column 17, line 45, change "such benzalkonium chloride," to -- such as benzalkonium chloride, --.

Column 18, line 17, change "Quatemium-15" to -- Quaternium-15 --.

Column 18, line 18, change "Quatemium-5" to -- Quaternium-5 --.

Column 18, line 19, change "Quatemium-22" to -- Quaternium-22 --.

Column 18, lines 32-33, change "propylenediarnine" to -- propylenediamine --.

Column 19, line 35, change "croscarnellose" to -- croscarmellose --.

Column 23, line 49, change "intracistemally" to -- intracisternally --.

Column 24, line 30, a period "." Should be added after the word "thereof".

Column 25, line 57, change "A G" to -- AG --.

Column 25, line 63, change "pyrrotidone" to -- pyrrolidone --.

UNITED STATES PATENT AND TRADEMARK OFFICE
CERTIFICATE OF CORRECTION

PATENT NO. : 7,276,249 B2
APPLICATION NO. : 10/444066
DATED : October 2, 2007
INVENTOR(S) : Tuula Ryde et al.

It is certified that error appears in the above-identified patent and that said Letters Patent is hereby corrected as shown below:

Table 13, change "µg/mL h" to -- µg/mL.h --.

Column 31, line 20, change "The relevant date" to -- The relevant data --.

Table 14, change "µg/mL h" to -- µg/mL.h --.

Table 15, change "µg/mL h" to -- µg/mL.h --.

Table 16, change "µg/mL h" to -- µg/mL.h --.

Column 33, line 12, change "table" to -- tablet --.

IN THE CLAIMS:

Claim 10, please delete "claim 136" and insert therefor -- claim 1 --.

Claim 15, please delete "6.5 g/mL" and insert therefor -- 6.5 µg/mL --.

Claim 55, please delete "eationic" and insert therefor -- cationic --.

Claim 56, please delete "n-noyl b-D-glucopyranoside" and insert therefor -- n-nonyl b-D-glucopyranoside --.

Claim 61, please delete "n-noyl b-D-glucopyranoside" and insert therefor -- n-nonyl b-D-glucopyranoside --.

Claim 62, please delete "quartemary ammonium compounds" and insert therefor -- quarternary ammonium compounds --.

Claim 73, please delete "claim 136" and insert therefor -- claim 64 --.

Claim 78, the period "." after the word "of" should be deleted.

Claim 83, please delete "3.0 g/mL" and insert therefor -- 3.0 µg/mL --.

UNITED STATES PATENT AND TRADEMARK OFFICE
CERTIFICATE OF CORRECTION

PATENT NO.        : 7,276,249 B2
APPLICATION NO.   : 10/444066
DATED             : October 2, 2007
INVENTOR(S)       : Tuula Ryde et al.

It is certified that error appears in the above-identified patent and that said Letters Patent is hereby corrected as shown below:

Claim 93, please delete "intracistemal" and insert therefor -- intracisternal --.

Claim 99, please delete "0.02 5 M" and insert therefor -- 0.025 M --.

Claim 118, please delete "n-noyl β-D-glucopyranoside" and insert therefor -- n-nonyl β-D-glucopyranoside --.

Claim 119, please delete "quartemary ammonium compounds" and insert therefor -- quarternary ammonium compounds --.

Claim 130, please delete "claim 136" and insert therefor -- claim 121 --.

Claim 150, please delete "intracistemal" and insert therefor -- intracisternal --.

Claim 175, please delete "n-noyl b-D-glucopyranoside" and insert therefor -- n-nonyl b-D-glucopyranoside --.

Claim 176, please delete "quartemary ammonium compounds" and insert therefor -- quarternary ammonium compounds --.

Claim 181, please delete "n-noyl b-D-glucopyrano side" and insert therefor -- n-nonyl b-D-glucopyranoside --.

Claim 182, please delete "quartemary ammonium compounds" and insert therefor -- quarternary ammonium compounds --.

Claim 187, please delete "n-noyl b-D-glucopyranoside" and insert therefor -- n-nonyl b-D-glucopyranoside --.

UNITED STATES PATENT AND TRADEMARK OFFICE
CERTIFICATE OF CORRECTION

PATENT NO. : 7,276,249 B2
APPLICATION NO. : 10/444066
DATED : October 2, 2007
INVENTOR(S) : Tuula Ryde et al.

It is certified that error appears in the above-identified patent and that said Letters Patent is hereby corrected as shown below:

Claim 188, please delete "quartemary ammonium compounds" and insert therefor -- quarternary ammonium compounds --.

Signed and Sealed this

Sixth Day of May, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,276,249 B2 |
| APPLICATION NO. | : 10/444066 |
| DATED | : October 2, 2007 |
| INVENTOR(S) | : Tuula Ryde et al. |

It is certified that error appears in the above-identified patent and that said Letters Patent is hereby corrected as shown below:

IN THE DRAWINGS:

In both Figures 1 and 2, please change "200 M LFF" to -- 200 mg LFF --.

Column 9, line 23, change "ice" to -- i.e., --.

Column 16, lines 53-54, change "benzyl-di(2-chloroethyl)etbylammonium bromide" to -- benzyl-di(2-choloroethyl)ethylammonium bromide --.

Column 16, line 31, please delete "n-noyl b-D-glucopyranoside" and insert therefor -- n-nonyl b-D-glucopyranoside --.

Column 17, line 33, change "acrylarnides" to -- acrylamides --.

Column 17, line 45, change "such benzalkonium chloride," to -- such as benzalkonium chloride, --.

Column 18, line 17, change "Quatemium-15" to -- Quaternium-15 --.

Column 18, line 18, change "Quatemium-5" to -- Quaternium-5 --.

Column 18, line 19, change "Quatemium-22" to -- Quaternium-22 --.

Column 18, lines 32-33, change "propylenediarnine" to -- propylenediamine --.

Column 19, line 35, change "croscarnellose" to -- croscarmellose --.

Column 23, line 49, change "intracistemally" to -- intracisternally --.

Column 24, line 30, a period "." Should be added after the word "thereof".

Column 25, line 57, change "A G" to -- AG --.

Column 25, line 63, change "pyrrotidone" to -- pyrrolidone --.

UNITED STATES PATENT AND TRADEMARK OFFICE
CERTIFICATE OF CORRECTION

| | |
|---|---|
| PATENT NO. | : 7,276,249 B2 |
| APPLICATION NO. | : 10/444066 |
| DATED | : October 2, 2007 |
| INVENTOR(S) | : Tuula Ryde et al. |

It is certified that error appears in the above-identified patent and that said Letters Patent is hereby corrected as shown below:

Table 13, change "µg/mL h" to -- µg/mL.h --.

Column 31, line 20, change "The relevant date" to -- The relevant data --.

Table 14, change "µg/mL h" to -- µg/mL.h --.

Table 15, change "µg/mL h" to -- µg/mL.h --.

Table 16, change "µg/mL h" to -- µg/mL.h --.

Column 33, line 12, change "table" to -- tablet --.

IN THE CLAIMS:

Column 35, line 56, Claim 10, please delete "claim 136" and insert therefor -- claim 1 --.

Column 36, line 29, Claim 15, please delete "6.5 g/mL" and insert therefor -- 6.5 µg/mL --.

Column 39, line 55, Claim 55, please delete "eationic" and insert therefor -- cationic --.

Column 40, line 18, Claim 56, please delete "n-noyl b-D-glucopyranoside" and insert therefor -- n-nonyl b-D-glucopyranoside --.

Column 41, line 50, Claim 61, please delete "n-noyl b-D-glucopyranoside" and insert therefor -- n-nonyl b-D-glucopyranoside --.

Column 41, line 63, Claim 62, please delete "quartemary ammonium compounds" and insert therefor -- quarternary ammonium compounds --.

Column 43, line 31, Claim 73, please delete "claim 136" and insert therefor -- claim 64 --.

UNITED STATES PATENT AND TRADEMARK OFFICE
CERTIFICATE OF CORRECTION

PATENT NO.      : 7,276,249 B2
APPLICATION NO. : 10/444066
DATED           : October 2, 2007
INVENTOR(S)     : Tuula Ryde et al.

It is certified that error appears in the above-identified patent and that said Letters Patent is hereby corrected as shown below:

Column 44, line 3, Claim 78, the period "." after the word "of" should be deleted.

Column 44, line 29, Claim 83, please delete "3.0 g/mL" and insert therefor -- 3.0 µg/mL --.

Column 45, line 7, Claim 93, please delete "intracistemal" and insert therefor -- intracisternal --.

Column 45, line 30, Claim 99, please delete "0.02 5 M" and insert therefor -- 0.025 M --.

Column 47, line 42, Claim 118, please delete "n-noyl β-D-glucopyranoside" and insert therefor -- n-nonyl β-D-glucopyranoside --.

Column 47, line 55, Claim 119, please delete "quartemary ammonium compounds" and insert therefor -- quarternary ammonium compounds --.

Column 49, line 23, Claim 130, please delete "claim 136" and insert therefor -- claim 121 --.

Column 50, line 64, Claim 150, please delete "intracistemal" and insert therefor -- intracisternal --.

Column 53, line 33, Claim 175, please delete "n-noyl b-D-glucopyranoside" and insert therefor -- n-nonyl b-D-glucopyranoside --.

Column 53, line 46, Claim 176, please delete "quartemary ammonium compounds" and insert therefor -- quarternary ammonium compounds --.

UNITED STATES PATENT AND TRADEMARK OFFICE
CERTIFICATE OF CORRECTION

PATENT NO.        : 7,276,249 B2
APPLICATION NO.   : 10/444066
DATED             : October 2, 2007
INVENTOR(S)       : Tuula Ryde et al.

It is certified that error appears in the above-identified patent and that said Letters Patent is hereby corrected as shown below:

Column 55, line 17, Claim 181, please delete "n-noyl b-D-glucopyrano side" and insert therefor -- n-nonyl b-D-glucopyranoside --.

Column 55, line 30, Claim 182, please delete "quartemary ammonium compounds" and insert therefor -- quarternary ammonium compounds --.

Column 57, line 1, Claim 187, please delete "n-noyl b-D-glucopyranoside" and insert therefor -- n-nonyl b-D-glucopyranoside --.

Column 57, line 14, Claim 188, please delete "quartemary ammonium compounds" and insert therefor -- quarternary ammonium compounds --.

This certificate supersedes the Certificate of Correction issued May 6, 2008.

Signed and Sealed this

Tenth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,276,249 B2  Page 1 of 1
APPLICATION NO. : 10/444066
DATED : October 2, 2007
INVENTOR(S) : Ryde et al.

It is certified that error appears in the above-identified patent and that said Letters Patent is hereby corrected as shown below:

BRIEF DESCRIPTION OF THE DRAWINGS:

Please correct the following error:

Column 6, line 35, please replace "minutes" with -- hours --.

Signed and Sealed this

Twenty-sixth Day of January, 2010

David J. Kappos
*Director of the United States Patent and Trademark Office*